United States Patent
Downs et al.

(10) Patent No.: US 6,827,113 B2
(45) Date of Patent: Dec. 7, 2004

(54) MASSIVELY PARALLEL FLUID DISPENSING SYSTEMS AND METHODS

(75) Inventors: Robert C. Downs, La Jolla, CA (US); Mark R. Weselak, San Diego, CA (US)

(73) Assignee: IRM, LLC, Hamilton (BM)

( * ) Notice: Subject to any disclaimer, the term of this patent is extended or adjusted under 35 U.S.C. 154(b) by 99 days.

(21) Appl. No.: 10/109,582

(22) Filed: Mar. 27, 2002

(65) Prior Publication Data

US 2002/0153055 A1 Oct. 24, 2002

Related U.S. Application Data

(63) Continuation-in-part of application No. 09/818,748, filed on Mar. 27, 2001, now Pat. No. 6,659,142.

(51) Int. Cl.[7] .................................................. B05C 1/00
(52) U.S. Cl. ........................ 141/234; 141/1; 141/101; 141/104; 141/130; 141/243
(58) Field of Search .................. 141/1, 2, 18, 100–102, 141/104, 130, 234–237, 242, 243; 422/100; 436/180

(56) References Cited

U.S. PATENT DOCUMENTS

| | | |
|---|---|---|
| 5,306,510 A | 4/1994 | Meltzer |
| 5,736,105 A | 4/1998 | Astle |
| 5,738,728 A | 4/1998 | Tisone |
| 5,741,554 A | 4/1998 | Tisone |
| 5,743,960 A | 4/1998 | Tisone |
| 5,916,524 A | 6/1999 | Tisone |
| 6,039,211 A | 3/2000 | Slater et al. |
| 6,063,339 A | 5/2000 | Tisone et al. |
| 6,296,673 B1 | 10/2001 | Santarsiero et al. |
| 6,372,185 B1 | 4/2002 | Shumate et al. |

FOREIGN PATENT DOCUMENTS

| | | |
|---|---|---|
| WO | WO 00/78445 A1 | 12/2000 |
| WO | WO 02/062484 A1 | 8/2002 |
| WO | WO 02/063027 A1 | 8/2002 |
| WO | WO 02/068157 A2 | 9/2002 |
| WO | WO 02/075277 A2 | 9/2002 |

*Primary Examiner*—Gregory L. Huson
*Assistant Examiner*—Peter deVore
(74) *Attorney, Agent, or Firm*—Timothy L. Smith; Christopher C. Sappenfield; Quine Intellectual Property Law Group, P.C.

(57) ABSTRACT

The present invention provides highly automated fluid delivery systems and related methods with significantly improved throughput relative to preexisting technologies. In particular, the invention relates to a fluid dispensing system that simultaneously produces multiple fluid mixtures on-the-fly in multiple multiwell plates. The invention also includes control system and machine software in addition to various systems and related methods for performing assorted downstream processes.

119 Claims, 9 Drawing Sheets

Fig. 2

| 25 (SS 49) Glycerol (80 %) | 26 (SS 39) Ethylene Glycol (100 %) | 27 (SS 121) Formate_Na (7 M) | 28 (SS 171) Spermine (0.1 M) | 29 (SS 172) Sodium Bromide (2 M) | 30 (SS 173) PEG MME 550 (60 %) | 31 (SS 174) PEG MME 5000 (40 %) | 32 (SS 175) PEG 4000 (40 %) |
|---|---|---|---|---|---|---|---|
| 17 (SS 215) Cacodylate_Na (1 M) | 18 (SS 20) CHES_Na (1 M) | 19 (SS 217) Citrate_Na3 (1.6 M) | 20 (SS 219) HEPES_Na (1 M) | 21 (SS 156) Malonate_Na 2 (4 M) | 22 (SS 223) MES_Na (0.5 M) | 23 (SS 225) Phosphate_K Dibasic (4 M) | 24 (SS 224) Phosphate_Na Monobasic (4 M) |
| 9 (SS 11) Na Cl (5 M) | 10 (SS 212) Acetic Acid (1 M) | 11 (SS 214) Cacodylic Acid (1 M) | 12 (SS 14) CHES (1 M) | 13 (SS 216) Citric Acid (1.6 M) | 14 (SS 218) HEPES (1 M) | 15 (SS 222) MES (0.5 M) | 16 (SS 167) Acetate_Na (5 M) |
| 1 (SS 1) WATER (100 %) | 2 (SS 162) Lithium Nitrate (3 M) | 3 (SS 163) Cobalt Chloride (0.5 M) | 4 (SS 164) Ferric_Chloride (0.5 M) | 5 (SS 155) Bicine (1 M) | 6 (SS 156) Bicine_Na (1 M) | 7 (SS 157) CAPS (1 M) | 8 (SS 158) CAPS_Na (1 M) |

| 57 (SS 134) PEG 400 (60 %) | 58 (SS 184) PEG 1000 (40 %) | 59 (SS 185) PEG 3000 (40 %) | 60 (SS 9) PEG 8000 (30 %) | 61 (SS 128) PEG MME 2000 (40 %) | 62 (SS 66) PEG 6000 (30 %) | 63 (SS 67) PEG 10000 (30 %) | 64 (SS 126) PEG 200 (60 %) |
|---|---|---|---|---|---|---|---|
| 49 (SS 213) Acetate_Na (1 M) | 50 (SS 179) Calcium Chloride (0.5 M) | 51 (SS 180) Malonic Acid (4 M) | 52 (SS 181) Tartaric Acid (1.6 M) | 53 (SS 182) Formate_NH4 (8 M) | 54 (SS 183) Formic Acid (8 M) | 55 (SS 144) Citrate 1 (1 M) | 56 (SS 145) Citrate 2 (1 M) |
| 41 (SS 35) Mg Cl (2 M) | 42 (SS 226) Tris Cl (1 M) | 43 (SS 37) Zn Acetate (1 M) | 44 (SS 177) Cobalt Hexamine (0.2 M) | 45 (SS 54) Li Cl (8 M) | 46 (SS 55) Spermidine (0.1 M) | 47 (SS 178) Strontium Chloride (0.5 M) | 48 (SS 41) Mg Acetate (2 M) |
| 33 (SS 27) Phosphate_NH4 Dibasic (3.5 M) | 34 (SS 28) Sulfate_Li (2 M) | 35 (SS 29) Sulfate_NH4 (3.5 M) | 36 (SS 176) Tartrate_Na2 (1.6 M) | 37 (SS 221) Imidazole (1 M) | 38 (SS 227) Tris_base (1 M) | 39 (SS 33) Acetate_Ca (1 M) | 40 (SS 220) Imidazole Chloride (1 M) |

| 89 (SS 119) 1_2-propanediol (80 %) | 90 (SS 207) DMSO (80 %) | 91 (SS 95) Methanol (50 %) | 92 (SS 96) Dioxane (50 %) | 93 (SS 208) Trifluoroethanol (50 %) | 94 (SS 209) MPD (60 %) | 95 (SS 4) Ethanol (95 %) | 96 #N/A Isopropanol #N/A |
|---|---|---|---|---|---|---|---|
| 81 (SS 199) Sucrose (50 %) | 82 (SS 200) Xylitol (50 %) | 83 (SS 201) Sorbitol (50 %) | 84 (SS 202) EDTA (0.2 M) | 85 (SS 203) Benzamidine (10 %) | 86 (SS 204) Benzylkonium Chloride (20 %) | 87 (SS 205) hexafluropropanol (50 %) | 88 (SS 206) 1_6-Hexanediol (80 %) |
| 73 (SS 191) Ammonium Iodide (0.5 M) | 74 (SS 192) Manganese Chloride (1 M) | 75 (SS 193) TCEP (0.1 M) | 76 (SS 194) UREA (2 M) | 77 (SS 195) Guanidine Hydrochloride (2 M) | 78 (SS 196) cyclohexyl-pentyl-B-D-maltoside(CYM 6) (0.01 M) | 79 (SS 197) Betaine (3 M) | 80 (SS 198) Sarcosine (3 M) |
| 65 (SS 127) PEG 300 (60 %) | 66 (SS 123) PEG 600 (60 %) | 67 (SS 125) PEG 1450 (50 %) | 68 (SS 186) Potassium Chloride (4 M) | 69 (SS 185) Acetic Acid (5 M) | 70 (SS 188) Ammonium Perrhenate (0.2 M) | 71 (SS 189) Sodium Thiocyanate (0.5 M) | 72 (SS 190) Sodium Fluoride (0.5 M) |

| Salt | Buffer | Precipitant |
|---|---|---|
| 0.02 M Calcium Chloride dihydrate | 0.1 M Sodium Acetate trihydrate pH 4.6 | 30% v/v 2-Methyl-2,4-pentanediol |
| 0.2 M tri-Sodium Citrate dihydrate | 0.1 M Tris Hydrochloride pH 8.5 | 0.4 M Potassium Sodium Tartrate tetrahydrate |
| 0.2 M Magnesium Chloride hexahydrate | 0.1 M HEPES - Na pH 7.5 | 0.4 M mono-Ammonium dihydrogen Phosphate |
| 0.2 M tri-Sodium Citrate dihydrate | 0.1 M Tris Hydrochloride pH 8.5 | 2.0 M Ammonium Sulfate |
| 0.2 M Ammonium Acetate | 0.1 M Sodium Cacodylate pH 6.5 | 30% v/v 2-Methyl-2,4-pentanediol |
| 0.2 M Ammonium Acetate | 0.1 M Sodium Cacodylate pH 6.5 | 30% w/v Polyethylene Glycol 4000 |
| 0.2 M Magnesium Chloride hexahydrate | 0.1 M tri-Sodium Citrate dihydrate pH 5.6 | 1.4 M Sodium Acetate trihydrate |
| 0.2 M tri-Sodium Citrate dihydrate | 0.1 M Sodium Acetate trihydrate pH 4.6 | 30% v/v iso-Propanol |
| 0.2 M Calcium Chloride dihydrate | 0.1 M tri-Sodium Citrate dihydrate pH 5.6 | 30% w/v Polyethylene Glycol 4000 |
| 0.2 M Ammonium Sulfate | 0.1 M HEPES - Na pH 7.5 | 30% w/v Polyethylene Glycol 4000 |
| 0.2 M Lithium Sulfate monohydrate | 0.1 M Tris Hydrochloride pH 8.5 | 1.0 M mono-Ammonium dihydrogen Phosphate |
| 0.2 M Magnesium Acetate tetrahydrate | 0.1 M HEPES - Na pH 7.5 | 30% v/v iso-Propanol |
| 0.2 M Ammonium Acetate | 0.1 M Sodium Cacodylate pH 6.5 | 30% v/v Polyethylene Glycol 400 |
| 0.2 M Ammonium Sulfate | 0.1 M HEPES - Na pH 7.5 | 28% v/v Polyethylene Glycol 400 |
| 0.2 M Magnesium Acetate tetrahydrate | 0.1 M Tris Hydrochloride pH 8.5 | 30% w/v Polyethylene Glycol 8000 |
| 0.2 M Sodium Acetate trihydrate | 0.1 M Sodium Cacodylate pH 6.5 | 1.5 M Lithium Sulfate monohydrate |
| 0.2 M Magnesium chloride hexahydrate | 0.1 M Tris Hydrochloride pH 8.5 | 30% Polyethylene Glycol 4000 |
| 0.2 M Calcium Chloride dihydrate | 0.1 M Sodium Acetate trihydrate pH 4.6 | 20% Polyethylene Glycol 8000 |
| 0.2 M Ammonium Acetate | 0.1 M Sodium Cacodylate pH 6.5 | 30% v/v iso-Propanol |
| 0.2 M tri-Sodium Citrate dihydrate | 0.1 M Tris Hydrochloride pH 8.5 | 25% w/v Polyethylene Glycol 4000 |
| 0.2 M Sodium Acetate trihydrate | 0.1 M HEPES - Na pH 7.5 | 30% v/v 2-Methyl-2,4-pentanediol |
| 0.2 M Ammonium Sulfate | 0.1 M Sodium Acetate trihydrate pH 4.6 | 30% w/v Polyethylene Glycol 4000 |
| 0.2 M Ammonium Sulfate | 0.1 M Imidazole pH 6.5 | 30% v/v Polyethylene Glycol 400 |
| 0.05 M mono-Potassium dihydrogen Phosphate | 0.1 M tri-Sodium Citrate dihydrate pH 5.6 | 20% v/v iso-Propano |
| 0.2 M Zinc Acetate dihydrate | 0.1 M HEPES - Na pH 7.5 | 1.0 M Sodiuml Acetate trihydrate |
| 0.2 M Calcium Acetate hydrate | 0.1 M Sodium Cacodylate pH 6. | 30 % v/v 2-Methyl-2,4-pentanediol |
| 1.0 M Lithium Sulfate monohydrate | 0.1 M HEPES - Na pH 7.55 | 20% v/v iso-Propanol |
| 0.5 M Lithium Sulfate monohydrate | 0.1 M Sodium Acetate trihydrate pH 4.6 | 30% w/v Polyethylene Glycol 8000 |
| | 0.1 M HEPES - Na pH 7.5 | 0.8 M Potassium Sodium Tartrate tetrahydrate |
| | 0.1 M Tris Hydrochloride pH 8.5 | 30% w/v Polyethylene Glycol 8000 |
| | 0.1 M Sodium Acetate trihydrate pH 4.6 | 30% w/v Polyethylene Glycol 4000 |
| | 0.1 M HEPES - Na pH 7.5 | 2.0 M Ammonium Sulfate |
| | 0.1 M HEPES - Na pH 7.5 | 4.0 M Sodium Formate |
| | 0.1 M tri-Sodium Citrate dihydrate pH 5.6 | 2.0 M Sodium Formate |
| | 0.1 M HEPES - Na pH 7.5 | 0.8 M mono-Sodium dihydrogen phosphate |
| | 0.1 M Sodium Cacodylate pH 6.5 | 0.8 M mono-Potassium dihydrogen phosphate |
| | 0.1 M Sodium Cacodylate pH 6.5 | 8% w/v Polyethylene Glycol 8000 |
| | 0.1 M Sodium Acetate trihydrate pH 4.6 | 8% w/v Polyethylene Glycol 4000 |
| | 0.1 M Tris Hydrochloride pH 8.5 | 1.4 M tri-Sodium Citrate dihydrate |
| | | 2% v/v Polyethylene Glycol 400, 2.0 M Ammonium Sulfate |
| | | 20% v/v iso-Propanol, 20% w/v Polyethylene Glycol 4000 |
| | | 10% v/v iso-Propanol, 20% w/v Polyethylene Glycol 4000 |
| | | 20% w/v Polyethylene Glycol 8000 |
| | | 30% w/v Polyethylene Glycol 1500 |
| | | 0.2 M Magnesium Formate |
| | | 18% w/v Polyethylene Glycol 8000 |
| | | 18% w/v Polyethylene Glycol 8000 |
| | | 2.0 M Ammonium Sulfate |
| | | 2.0 M mono-Ammonium dihydrogen Phosphate |
| | | 2% w/v Polyethylene Glycol 8000 |
| | | 15% w/v Polyethylene Glycol 8000 |

Fig. 9

MASSIVELY PARALLEL FLUID DISPENSING SYSTEMS AND METHODS

CROSS-REFERENCES TO RELATED APPLICATIONS

This application is a continuation-in-part of U.S. patent application Ser. No. 09/818,748, filed on Mar. 27, 2001, now U.S. Pat. No. 6,659,142 entitled "APPARATUS AND METHOD FOR PREPARING FLUID MIXTURES," by Downs et al., the disclosure of which is incorporated by reference. The present application claims priority to and the benefit of this related application, pursuant to 35 U.S.C. § 119, 35 U.S.C. § 120, and any other applicable statute or rule.

COPYRIGHT NOTIFICATION

Pursuant to 37 C.F.R. § 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

STATEMENT AS TO RIGHTS TO INVENTIONS MADE UNDER FEDERALLY SPONSORED RESEARCH AND DEVELOPMENT

Not Applicable.

FIELD OF THE INVENTION

The present invention relates to fluid dispensing systems. More specifically, the invention provides automated systems for simultaneously producing multiple fluid mixtures in multiple multiwell plates with high throughput.

BACKGROUND OF THE INVENTION

Acquiring knowledge of the detailed three-dimensional structures of proteins and other macromolecules is central to structure-based drug development. A prominent methodology for solving high-resolution molecular structure is x-ray crystallography, which entails crystallizing the molecule under consideration. The process typically involves crystallizing a test sample that includes the target molecule in a fluid mixture formulated to provide stable and highly ordered crystals. The art of crystallization, however, is often difficult and time consuming. For example, each new protein crystallization generally requires a unique concentration and mixture of salts, precipitants, and other fluids for crystal growth to occur. It is typically necessary to screen a protein sample against hundreds or even thousands of varied fluid mixtures or crystallization mother liquors in order to identify the proper combination of fluids that will yield a crystallized form of the protein. To further illustrate, finding the proper fluid mixture may require varying the composition of the mixture using a multi-dimensional array of variables, such as different types of aqueous, salt, precipitant, organic, and buffer solutions, different concentrations and pH levels for those fluids, different atmospheric conditions, and the like.

Screens for suitable crystallization conditions are currently conducted manually using skilled technicians. Performing each screen is generally a labor intensive process, in part, because the different fluid mixtures into which the target molecules are deposited must themselves be dispensed, e.g., in very small amounts into the wells of multiwell plates, such as microwell plates. The physical act of dispensing these small amounts into such small fluid containers is itself a time consuming and inaccurate process. In addition, the amount of test sample available for each individual screen is often limited. Further, the screening fluids used in each screen are typically measured in microliter volumes or less. This requires a high level of precision and accuracy that can be difficult even for skilled technicians. The reliability and reproducibility of each screen are integral to the precision and accuracy of the screens. Accordingly, there exists a need to automate the screening process to increase throughput, and to increase the level of precision, accuracy, and reproducibility of the process.

As mentioned, conventional crystallization techniques generally require that each test sample to be crystallized be screened against numerous different fluid mixtures in order to find a proper composition that provides stable crystallization conditions for the particular target molecule in question. In a manual screening process, a technician is primarily responsible for measuring, mixing, and dispensing each unique fluid mixture. Such a manual process is time consuming and expensive, and therefore the variations of fluid mixtures are often limited because of time constraints in the screening process. Unfortunately, by reducing the granularity of the screen, a less than optimum fluid mixture will likely be selected. Further, such a manual screening process is highly susceptible to human mathematical and measurement errors in fluid preparation. As a consequence, the screen may yield erroneous, unreliable, and non-reproducible results.

Yet another problem associated with screening crystallization conditions is that many of the component fluids of crystallization mother liquors used in the screens are highly volatile. These volatile fluids can evaporate or change in character rapidly in a short period of time. Therefore, it is often difficult to manually prepare a screen that includes a large number of individual crystallization assays due to the time required to deposit the fluids into each well. As the different fluids are deposited in each well, the volatile fluids can evaporate or otherwise change composition, rendering the particular screen inaccurate or otherwise biased.

From the above, it is apparent that there is a substantial need for fluid dispensing systems that simultaneously produce multiple fluid mixtures (e.g., mother liquor solutions for crystallization screens, etc.) in multiple multiwell plates. These and a variety of additional features of the present invention will become evident upon complete review of the following disclosure.

SUMMARY OF THE INVENTION

The present invention provides highly automated fluid delivery systems and related methods with significantly improved throughput relative to preexisting technologies. In particular, the invention relates to a fluid dispensing system that simultaneously produces multiple fluid mixtures on-the-fly in multiple multiwell plates. The invention also includes software that, inter alia, directs fluid dispensing from multiple fluid dispensers and tracks fluid mixture compositions in the wells of multiwell plates. In addition, various systems and related methods are also provided for performing assorted downstream processes. Fluid mixtures prepared utilizing the systems and methods described herein are useful for essentially any purpose including, for example, preparation of mother liquor solutions for high throughput crystallization screens.

The present invention provides a fluid dispensing system that includes an array of fluid dispensers. In some embodiments, the array includes at least two fluid dispensers that are spaced at least a sufficient distance apart to simultaneously dispense a fluid into a well of a first multiwell plate and a corresponding well of a second multiwell plate when both plates are placed beneath the array of fluid dispensers. The number of fluid dispensers in the array is, in certain embodiments, at least as great as the number of wells in two lines of wells of a single multiwell plate; and in these embodiments the fluid dispensers are spaced an appropriate distance apart from one another to simultaneously dispense a fluid into wells of multiple multiwell plates when the plates are placed underneath the fluid dispensers. In some configurations, the array of fluid dispensers includes a plurality of linear arrays, each of which comprises at least two fluid dispensers that are spaced at least a sufficient distance apart to simultaneously dispense a fluid into a well of a first multiwell plate and a corresponding well of a second multiwell plate when both plates are placed beneath the array of fluid dispensers.

In one aspect, the present invention provides a fluid dispensing system that includes a linear array of fluid dispensers in which the linear array includes a number of fluid dispensers that is greater than the number of wells in a line of wells (e.g., a row or column of wells) of a single multiwell plate, which line of wells is parallel to a longitudinal axis of the linear array. Each dispenser is spaced an appropriate distance apart from an adjacent fluid dispenser to allow the two adjacent dispensers to simultaneously dispense a fluid into adjacent wells of a multiwell plate when the multiwell plate is placed underneath the fluid dispensers. Suitable spacings include, but are not limited to, 144 mm, 72 mm, 36 mm, 18 mm, 9 mm, 4.5 mm, 2.25 mm or less (center to center), depending upon the plate format. In some embodiments, the number of fluid dispensers is x times the number of wells in the line of wells of a single multiwell plate and x is a whole number greater than or equal to 2 (e.g., 3, 4, 5, 6, 7, 8, 9, 10, or more), although other configurations can be utilized. Typically, each of the fluid dispensers is connected to a fluid container that contains a different fluid (e.g., a different stock solution, such as water, a precipitant or polymer solution, a buffer, an organic solution, or the like) for producing varied mixtures of crystallization mother liquor solutions. Furthermore, although other volumes are optionally dispensed, each fluid dispenser separately generally dispenses selected volumes between about 1 nl and about 500 µl. The linear array of fluid dispensers is optionally configured so that the fluid dispensers can deliver fluid to at least two, at least three, at least four, or more multiwell plates at the same time.

To illustrate, the adjacent dispensers are optionally spaced an appropriate distance apart to allow the adjacent fluid dispensers to simultaneously dispense a fluid into adjacent wells of a 96-well plate. For example, if the line of wells that is parallel to a longitudinal axis of the linear array includes eight wells, then the linear array comprises at least nine fluid dispensers. In contrast, if multiwell plate is oriented such that the line of wells that is parallel to the longitudinal axis of the linear array includes twelve wells, then the linear array comprises at least thirteen fluid dispensers. For example, the linear array optionally includes various numbers of fluid dispensers (e.g., at least 17 fluid dispensers, at least 25 fluid dispensers, at least 33 fluid dispensers, etc.). In some embodiments, the linear array includes 96 fluid dispensers.

In some embodiments, the fluid dispensing system includes an array of fluid dispensers comprising more than 12 fluid dispensers aligned with each other along a longitudinal axis such that two adjacent fluid dispensers can each dispense a fluid into a different adjacent well of a multiwell plate positioned stationary underneath the array of fluid dispensers; and a mechanism for moving the array of fluid dispensers and a multiwell plate positioned underneath the array of fluid dispensers relative to each other in a direction perpendicular to the longitudinal axis. The fluid dispensing systems can include, for example, 16, 24, 48, 60, 96, or more fluid dispensers aligned with each other along a longitudinal axis. The fluid dispensers in the fluid dispensing system are, in some embodiments, in fluid connection with at least 8 different fluid sources. For example, the fluid dispensers can be in fluid connection with 8, 16, 24, 48, 60, 96 or more different fluid sources. The fluid dispensers can, in some embodiments of the fluid dispensing system, deliver fluid to wells of at least three different multi-well plates at the same time. For example, the invention provides fluid dispensing systems in which the fluid dispensers can deliver fluid to wells of 3, 4, 5, 6, or more different multi-well plates at the same time.

In certain embodiments, at least a first fluid dispenser in the array is connected to a fluid container that contains a first fluid and at least a second fluid dispenser in the array is connected to a fluid container that contains a second fluid that differs from the first fluid. Adjacent fluid dispensers typically dispense different fluids. For example, the first and second fluids are independently selected from, e.g., water, a stock solution, a buffer, a reagent, a solvent, a salt solution, a polymer solution, an inorganic solution, an organic solvent, a cell suspension, or the like. In some embodiments, at least a first fluid dispenser in the array is connected to a fluid container that contains water, at least a second fluid dispenser in the array is connected to a fluid container that contains a salt solution, at least a third fluid dispenser in the array is connected to a fluid container that contains a polymer solution, and at least a fourth fluid dispenser in the array is connected to a fluid container that contains an organic solvent. The salt solution optionally includes one or more components selected from, e.g., cacodylic acid, CHES, HEPES, citric acid, malonic acid, MES, phosphoric acid, acetic acid, a salt thereof, or the like. The polymer solution optionally includes one or more components selected from, e.g., glycerol, ethylene glycol, formate, spermine, polyethylene glycol, or the like. The organic solvent optionally includes one or more components selected from, e.g., 1,2-propanediol, DMSO, methanol, dioxane, trifluoroethanol, MPD, ethanol, isopropanol, or the like. In certain embodiments, each of these salt solutions, polymer solutions, and organic solvents is contained in at least one fluid container which is connected to a fluid dispenser in the array.

At least one, but typically each, of the fluid dispensers includes (i) a fluid conduit (e.g., a flexible tube or the like) in fluid communication with a fluid source or reservoir, and (ii) a pump (e.g., a peristaltic pump, a syringe pump, etc.) operably connected to the fluid conduit to convey fluid through the fluid conduit from the fluid source to the wells of the multiwell plates. In addition, each of the fluid dispensers generally includes a solenoid valve or a piezoelectric valve that operates in coordination with the pump to dispense selected volumes of fluid.

In preferred embodiments, a fluid dispensing system of the invention also includes a moving element (e.g., a conveyor belt, etc.) that moves the multiwell plates in a direction parallel to a longitudinal axis of the array of the fluid dispensers (e.g., in an x-axis direction). Optionally, the moving element moves reversibly (e.g., either in a positive or negative x-axis direction) at a given time. The moving element typically has a length of at least n of the multiwell plates, wherein n is the number of the multiwell plates. In certain embodiments, for example, n is a whole number selected from the group consisting of 2, 3, 4, 5, 6, 7, 8, 9, 10, or more. In addition, the array of fluid dispensers typically includes a support structure that is operably connected to a drive mechanism (e.g., a stepper motor, a servo motor, or the like) that reversibly moves the support structure in a direction perpendicular to a direction of movement of the moving element (e.g., in a positive or a negative y-axis direction at a given time). Optionally, fluid dispensing systems further include one or more cleaning devices to clean the fluid dispensers. Fluid dispensing systems also optionally include one or more waste containers into which volumes of waste fluid are dispensed from the dispensers.

A fluid dispensing system of the invention generally further includes a controller that is operably connected to the fluid dispensers, the moving element, and the drive mechanism, which controller controls at least fluid dispensation from the fluid dispensers, moving element movement, and support structure movement. The controller typically includes a logic device and a database. The logic device generally includes control system software and machine software in which the control system software communicates with the machine software and the database to control execution of the machine software. In addition, the machine software typically includes one or more logic instructions that direct the fluid dispensing system to, e.g., move the moving element a selected distance, move the support structure a selected distance, and dispense selected volumes of fluids from selected fluid dispensers into selected wells of the multiwell plates. Optionally, the logic instructions direct the fluid dispensing system to (a) sequentially position each well of two or more multiwell plates underneath each of the fluid dispensers, and (b) dispense selected volumes of fluid from selected fluid dispensers into selected wells of the multiwell plates when the selected fluid dispensers are positioned above the selected wells, thereby simultaneously producing multiple fluid mixtures in two or more multiwell plates. The system control logic can direct when fluid is dispensed from a given fluid dispenser to a well of a multiwell plate based on a position of the multiwell plate in the system. For some or all wells in a particular row, the selected volume dispensed by a selected fluid dispenser can be zero if the fluid mixture being prepared in that well is not intended to contain the fluid being dispensed by that fluid dispenser.

As an additional option, the logic instructions direct the fluid dispensing system to position a first well of a first row of a multiwell plate under a first fluid dispenser, move the support structure sequentially across the entire first row of a multi-well plate, dispensing selected volumes of a first fluid from the first fluid dispenser into one or more selected wells in the first row when the first fluid dispenser is positioned above the selected well, sequentially advance the moving element to position a first well of a second row of a multiwell plate under the first fluid dispenser and the first well of the first row under a second fluid dispenser, and move the support structure sequentially across the entire first and second rows, dispensing selected volumes of a first fluid from the first fluid dispenser into one or more selected wells in the second row when the first fluid dispenser is positioned above the selected well, and dispensing selected volumes of a second fluid from the second fluid dispenser into one or more selected wells in the first row when the second fluid dispenser is positioned above the selected well. The database typically includes information about, e.g., fluids in fluid containers that are in fluid communication with the fluid dispensers, selected wells into which a selected fluid dispenser is to dispense a selected fluid in which the selected wells are located on two or more multiwell plates, and selected volumes of the selected fluids that are to be dispensed into each selected well.

In another aspect, the present invention relates to methods of simultaneously producing multiple fluid mixtures in multiple multiwell plates. The methods include (a) providing a fluid dispensing system that includes an array of fluid dispensers, wherein the array comprises at least two fluid dispensers that are spaced at least a sufficient distance apart to simultaneously dispense a fluid into a well of a first multiwell plate and a corresponding well of a second multiwell plate when both plates are placed beneath the array of fluid dispensers. In some embodiments, the method uses a fluid dispensing system that includes a linear array of fluid dispensers in which each dispenser is spaced an appropriate distance apart from an adjacent dispenser to allow the two adjacent dispensers to simultaneously dispense a fluid into adjacent wells of a multiwell plate, and the number of fluid dispensers in the linear array is greater than the number of wells in a line of wells (e.g., a row or column of wells) of the multiwell plate that is parallel to a longitudinal axis of the linear array. The number of fluid dispensers, in some embodiments, is x times the number of wells in the line of wells of the multiwell plate and x is a whole number greater than or equal to 2 (e.g., 3, 4, 5, 6, 7, 8, 9, 10, or more), although this relationship between number of wells and number of fluid dispensers is not required. The methods also include (b) sequentially positioning each well of the multiple multi well plates underneath each of the fluid dispensers. In addition, the methods include (c) dispensing selected volumes (e.g., between about 1 nl and about 500 $\mu$l) of fluid from selected fluid dispensers into selected wells of the multiple multiwell plates when the selected fluid dispensers and the selected wells are positioned above the selected wells to simultaneously produce the multiple fluid mixtures in the multiple multiwell plates. In preferred embodiments, each of the fluid dispensers dispenses a different fluid. Generally, one or more of the fluid mixtures include 2, 3, 4, 5, 6, 7, 8, 9, 10, or more mixed fluids. In certain embodiments, the methods further include cleaning the fluid dispensers after one or more of the selected volumes are dispensed and/or dispensing volumes of waste fluid from the fluid dispensers into waste containers that correspond to linearly arrayed portions of the fluid dispensers.

In another aspect, the invention features a system for efficiently preparing mother liquors in a plurality of multi-well sample plates for, e.g., a coarse screen or a fine screen, in a plurality of sample plates. The plurality of sample plates is arranged with corresponding columns aligned, the system including: (a) a plate arranging area configured to receive the plurality of sample plates; (b) a plurality of fluid containers, each fluid container holding a stock solutions; (c) a plurality of fluid dispensers arranged in an array, each fluid dispenser being in fluid communication with an associated one of the fluid containers; (d) a drive mechanism constructed to sequentially position the fluid dispensers in the array directly over each column of wells in the sample plate; (e) a dispensing mechanism associated with each fluid dispenser; and (f) a fluid controller communicating to the dispensing mechanism in which the fluid controller directs selected dispensing mechanisms to deliver a quantity of each associated mother liquor into each selected sample well in a column before the drive mechanism moves the fluid dispenser array to a next column.

In preferred embodiments the plurality of fluid dispensers are configured so that 2, 3, 4, 5, 6, 7 or 8 sample plates can be beneath the plurality of fluid dispensers at the same time. The plurality of fluid dispensers preferably are configured so that the fluid dispensers can deliver the material to 2, 3, 4, 5, 6, 7 or 8 sample plates at the same time. The plurality of fluid dispensers may be configured so that all of the fluid dispensers can deliver the material at the same time. In one preferred embodiment, the system includes a moving element that has a length of at least n sample plates, wherein n is the number of sample plates, wherein each sample plate has m wells, wherein m is the number of wells, wherein the system processes a sample plate every m dispensings even though the sample plate is in the system for n times m dispensings. For example, the moving element has a length of at least five sample plates, wherein each sample plate has 96 wells, wherein the system processes a sample plate every 96 dispensings, even though the sample plate is in the system for 480 dispensings. The fluid controller preferably directs the delivery of the material from each fluid container to each sample plate, for example, the dispenser controller directs the delivery of the material from each of at least eight fluid containers to each of at least five multi-well plates.

In another aspect, the present invention provides a method for automatically preparing a mixture in a well of a multi-well holder. The method involves the steps of: (a) moving the multi-well holder so that the well is positioned below a fluid dispensing device; (b) dispensing fluid from the fluid dispensing device into the well; and (c) repeatedly moving the multi-well holder so that the well is positioned below a next fluid dispensing device and dispensing fluid from the next fluid dispensing device into the well until a predetermined mixture is prepared.

In preferred embodiments, the plurality of fluid dispensers are configured so that 2, 3, 4, 5, 6, 7 or 8 multi-well holders can be beneath the plurality of fluid dispensers at the same time. The plurality of fluid dispensers preferably are configured so that the fluid dispensers can deliver the material to 1, 2, 3, 4, 5, 6, 7 or 8 multi-well holders at the same time. The plurality of fluid dispensers may be configured so that all of the fluid dispensers can deliver the material at the same time. In one preferred embodiment, the sample plates are on a moving element that has a length of at least n sample plates, wherein n is the number of multi-well plates, wherein each multi-well plate has m wells, wherein m is the number of wells, wherein the method processes a multi-well plate every m dispensings even though the method involves n times m dispensings. For example, the sample plates are on a moving element that has a length of at least five multi-well plates, wherein each multi-well plate has 96 wells, wherein the method processes a multi-well plate every 96 dispensings, even though the method involves 480 dispensings. Preferably, a controller directs the delivery of the material from one or more fluid containers to each sample plate. For example, the controller directs the delivery of the material from each of at least eight fluid containers to each of at least five multi-well plates.

Finally, in another aspect, the present invention provides a fluid dispenser array for dispensing liquid into a plurality of multi-well sample plates. The fluid dispenser array includes a plurality of N fluid dispensers coupled into a linear array. N is a whole number multiple of the number of sample wells in one line of each sample plate. Each sample plate includes sample wells organized in a geometric pattern. The line may be a row or a column. By way of example, the number of sample wells in a line may be 12 and N may be 96.

In preferred embodiments of any of the aspects of the invention described herein, the footprint of the tubes in the column direction (i.e., the column length footprint) of the multi-well holder is at least 5.030, 10.060, 15.090, 20.120, 25.150, 30.180, 35.210, 40.240, or 45.270 inches long.

It readily will be appreciated that an advantage of the present system is to increase the speed, accuracy and reliability of protein crystallization and processing operations.

BRIEF DESCRIPTION OF THE DRAWINGS

The nature, goals, and advantages of the invention will become more apparent to those skilled in the art after considering the following detailed description when read in connection with the accompanying drawings in which like reference numerals identify like components throughout the drawings. It will be understood that some or all of the figures may be schematic representations for purposes of illustration and do not necessarily depict the actual relative sizes or locations of the elements shown.

FIG. 2 is a chart that lists 96 stock solutions from which fluid mixtures can be produced according to one embodiment of the invention.

FIG. 9 includes lists of salt, buffer, and precipitant solutions that are optionally used to prepare mother liquor solutions according to the methods described herein.

DETAILED DISCUSSION OF THE INVENTION

1. Definitions

Figure 1:
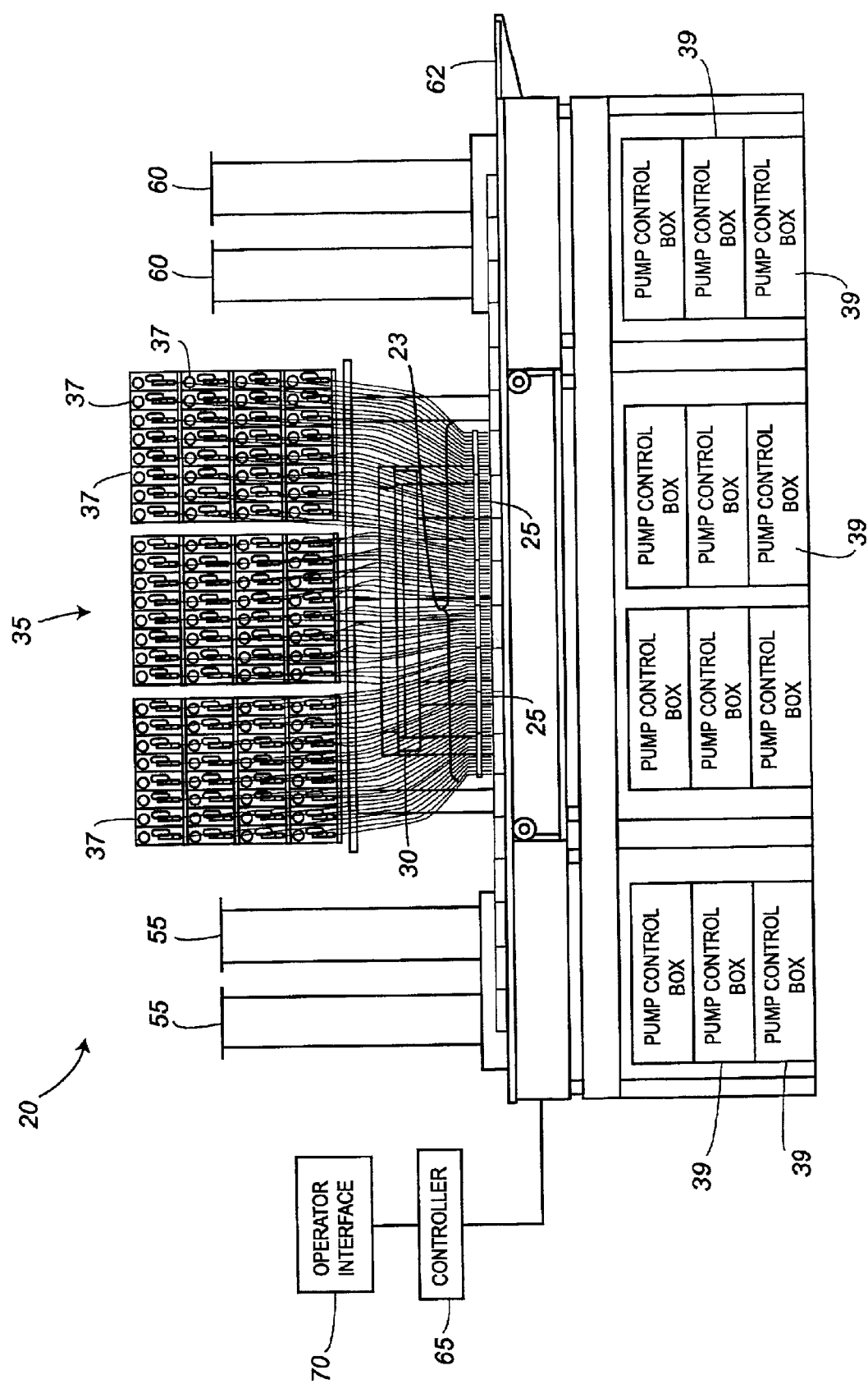
FIG. 1 schematically depicts one embodiment of a fluid dispensing system from a front elevational view.

Before describing the present invention in detail, it is to be understood that this invention is not limited to particular devices or systems, which can, of course, vary. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which the invention pertains. In describing and claiming the present invention, the following terminology will be used in accordance with the definitions set out below.

A "linear array" refers to an ordered, regular, or spatially defined pattern, grouping, or arrangement of components that is organized substantially as a straight line. For example, a linear array of fluid dispensers in a system of the present invention includes a number of fluid dispensers, or portions thereof, organized in a substantially straight line (e.g., disposed within a support structure or the like) such that each dispenser is spaced an appropriate distance apart from an adjacent dispenser to allow the two adjacent dispensers to simultaneously dispense a fluid into adjacent wells of a multiwell plate. Further, the number of fluid dispensers in these linear arrays is greater than the number of wells in each line of wells of a single multiwell plate. In certain embodiments of the invention, support structures include multiple linear arrays of fluid dispensers to simultaneously dispense fluids to multiple lines of wells in multiple multiwell plates.

A "footprint" refers to the area on a surface covered by or corresponding to a device component or portions thereof. For example, linearly arrayed fluid dispensers (e.g., dispenser tips of the fluid dispensers) of the invention typically correspond to (e.g., fit into, match, align with, etc.) wells in selected multiwell plates.

The term "massively parallel fluid dispensing" refers to the capability of simultaneously delivering multiple fluids to multiple wells in multiple microwell plates. In a preferred embodiment of a massively parallel fluid dispensing system of the invention, for example, the system includes a linear array of 96 fluid dispensers, each of which fluidly communicates with a different fluid container, such that as many as 96 different fluids can be dispensed simultaneously to 96 different wells disposed in, e.g., 8 or 12 different 96-well multiwell plates depending upon the orientation of the plates relative to the linear array.

A well of a multiwell plate is said to "correspond to" a well of a second multiwell plate when both wells are in the same location relative to the other wells of the respective plate. For example, a well at position A1 of a first plate corresponds to the well at position A1 of a second plate.

The term "processed multiwell plate" refers to a multiwell plate after fluid mixtures have been dispensed utilizing a fluid dispensing system of the invention.

The term "test sample" applies to a sample that contains a crystallization target molecule of interest. A test sample can also contain at least a second molecule that is to be co-crystallized with the target molecule. To perform a co-crystallization, the crystallization target in a test sample can be combined with at least one additional molecule such as, for example, a lipid, a nucleic acid, a compound, a protein, an antibody, a saccharide, a lipoprotein, a glycoprotein, an enzyme, or an antibody or fragment thereof, or any combination thereof, that can form a complex with the crystallization target. The term "co-crystallization" refers to crystallization of two or more molecules in a pre-existing complex (for example, an enzyme and a small molecule inhibitor). Alternatively, one can crystallize a macromolecule and 'soak' in the second molecule into the pre-existing crystal to form a complex. Soaking experiments can be achieved by adding the second molecule into the drop in which the macromolecule crystal is present, allowing the second molecule to diffuse into the crystal. Soaking and co-crystallization are two different approaches to achieving complexes between molecules.

II. Massively Parallel Fluid Dispensing Systems

The present invention provides systems for simultaneously producing multiple fluid mixtures in multiple multiwell plates. Significant advantages of these systems include increased throughput and flexibility relative to pre-existing technologies. For example, conventional approaches to fluid dispensing typically involve multiple fluid handlers. Further, conventional fluid dispensers are not designed to achieve massively parallel fluid dispensing as described herein. Some of these other dispensing devices are described in, e.g., U.S. Pat. No. 6,063,339, entitled "METHOD AND APPARATUS FOR HIGH-SPEED DOT ARRAY DISPENSING," which issued May 16, 2000 to Tisone et al., which is incorporated by reference in its entirety for all purposes.

More specifically, the present invention provides systems for producing fluid mixtures for essentially any type of process that utilizes, e.g., small volume mixtures of stock solutions. The mixtures include separate liquid components (e.g., stock solutions, etc.) that are used as a liquid medium for any process (e.g., biological process, chemical process, etc.). In preferred embodiments, the systems described herein are utilized to generate mother liquors for coarse and/or fine screen microcrystallization processes. The mother liquors are typically mixed in a 96-well (8 column× 12 row) format multiwell plate (e.g., a protein crystallization plate available from Hampton Research (Laguna Niguel, Calif.) or the like). It is to be noted that although the 96-well format is emphasized herein for purposes of clarity of illustration, the systems described herein are optionally adapted to essentially any other type of multiwell plate (e.g., plates with 6, 12, 24, 48, 384, 1536, or other numbers of wells) or other substrates.

The multiple 96-well plates move in a continuous stream along a moving element in a 9 mm step-by-step or indexed fashion underneath and parallel to a linear array of 96 fluid dispensers in which adjacent dispensers are also spaced 9 mm apart. In this way, each well of every plate in a particular row or column spends at least one time period underneath each of the dispense heads or tips in the linear array. At each forward step, the linear array also steps across the plates to cover all the wells of the plates. At each step, the control system decides which of the 96 stock solutions to dispense and how much of each stock solution should be dispensed into the wells that the linear array of dispensers is currently positioned over. Each well may contain any or all of the 96 stock solutions in essentially any combination of volumes once the particular plate had been processed. To further illustrate, although the time to get a particular plate through this embodiment of the system (i.e., residence time) involves 768 steps (96×8), the frequency with which plates emerge from the system is one very 96 steps (12×8).

Referring now to FIG. 1, an embodiment of a massively parallel fluid dispensing system is schematically shown from a front elevational view. In particular, multi-fluid dispensing system 20 is an automated system for handling, dispensing, and storing fluids. Essentially any fluid is optionally dispensed from multi-fluid dispensing system 20, such as water, stock solutions, buffers, reagents, solvents, salt solutions, polymer solutions, precipitant solutions, inorganic solutions, organic solutions, cell suspensions, or the like are optionally dispensed. In preferred embodiments, different mixtures of stock solutions are prepared as "mother liquors" for the growth of polypeptide or protein crystals. FIG. 2 is a chart that lists 96 exemplary stock solutions from which fluid mixtures can be produced according to one embodiment of the invention. As shown, solutions numbered 9–24 and 33–56 are salts, solutions numbered 25–32 and 57–64 are polymers, solutions 89–96 are organics, and solutions numbered 2–8 and 65–88 are other types of solutions. Exemplary stock solutions (e.g., salts, buffers, and precipitants) that are optionally used with the systems and methods described herein are also provided in FIG. 9 and in, e.g., in International Patent Publication WO 0018445, published Dec. 28, 2000 and in U.S. Pat. No. 6,296,673, entitled "METHODS AND APPARATUS FOR PERFORMING ARRAY MICROCRYSTALLIZATIONS," issued Oct. 2, 2001 to Santarsiero et al., which are both incorporated by reference in their entirety for all purposes. Many of these and other stock solutions are commercially available in ready-to-use formulations or can be easily prepared by those of skill from component chemical species. Certain commercial suppliers of these solutions, or components thereof, include, e.g., Emerald BioStructures, Inc. (Bainbridge Island, Wash.), Hampton Research (Laguna Niguel, Calif.), Sigma Chemical Company (St. Louis, Mo.), and the like. Although the illustrated examples are used to prepare fluid mixtures for screening protein crystallization mixtures, the apparatus and method for preparing fluid mixtures may be used for other purposes and in other fields.

Figure 5:
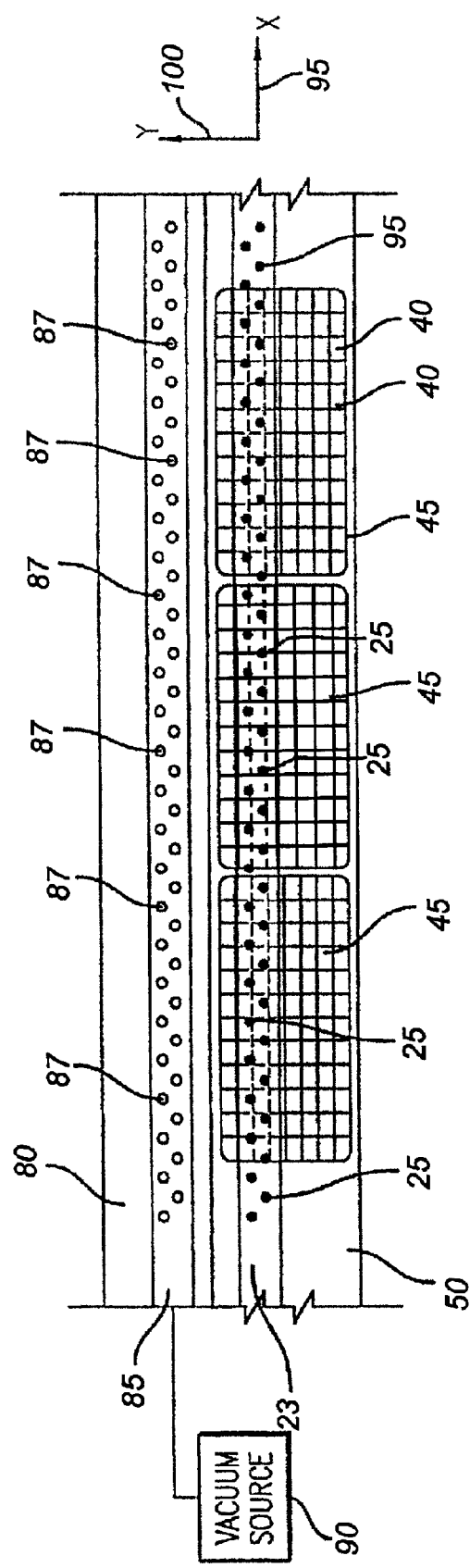
FIG. 5 schematically shows a segment of a support structure that includes two staggered linear arrays of dispensing tips disposed over multiple multiwell plates from a top view according to one embodiment of the invention.

Multi-fluid dispensing system 20 comprises a plurality of fluid dispensing tubes 25 mounted in tube array 23 (e.g., in a support structure or the like). The tube array is attached to a tube transport 30. In one embodiment, 96 tubes 25 are mounted to the tube array 23 in a single row. Different numbers of tubes 25 mounted in a different arrangement on the tube array 23 can be employed. For example, as shown in FIG. 5, a plurality of tubes 25 are mounted in a staggered configuration on tube array 23.

Figure 3:
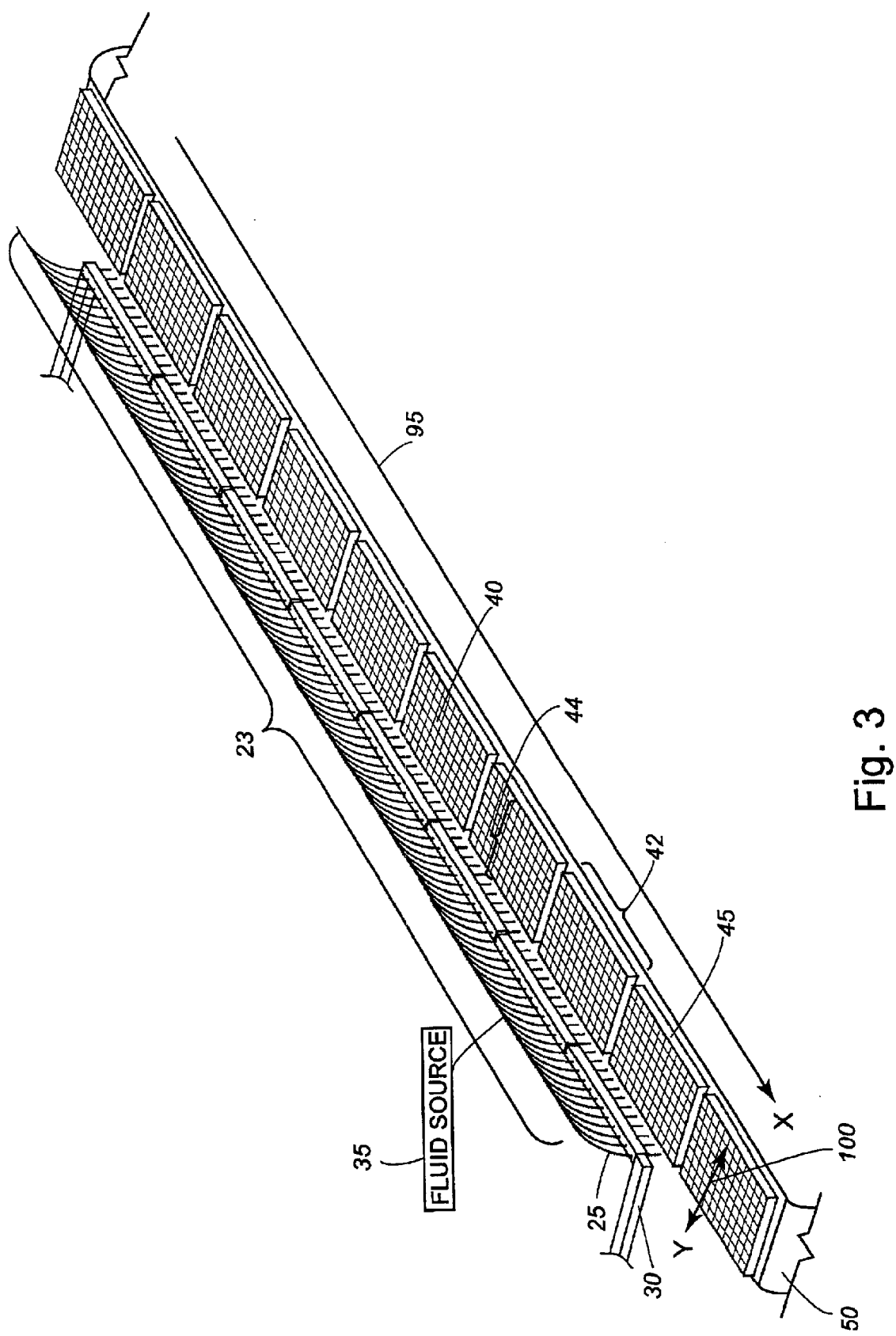
FIG. 3 schematically shows a support structure that includes linearly arrayed dispensing tips disposed over multiple multiwell plates on a moving element from a perspective view according to one embodiment of the invention.
Figure 4:
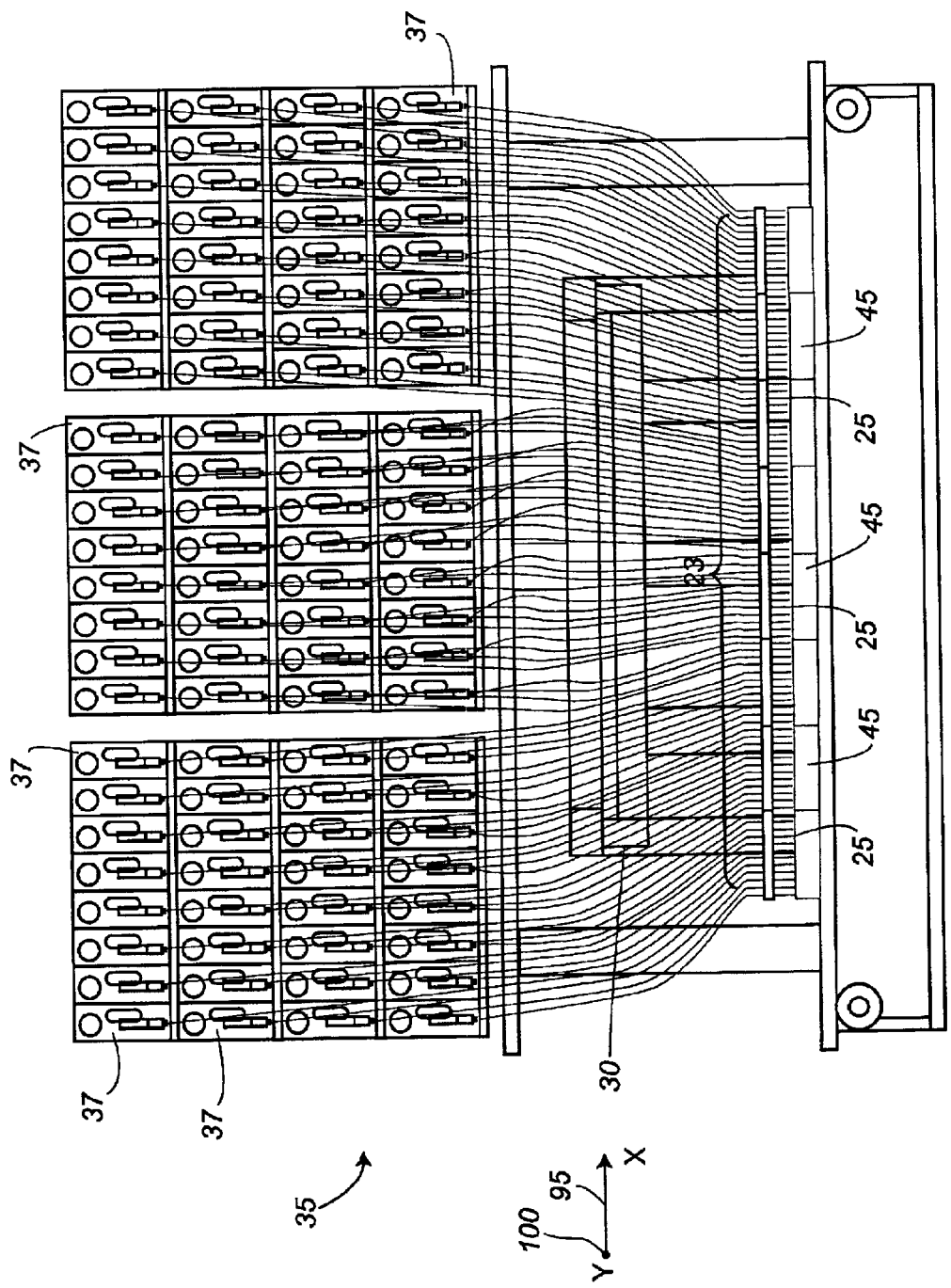
FIG. 4 schematically illustrates a support structure that includes 96 linearly arrayed dispensing tips and 96 syringe pumps from an elevational view according to one embodiment of the invention.

Referring also to FIGS. 3 and 4, tube transport 30 mounts the tube array so that the plurality of tubes are aligned with a moving element 50 (e.g., a conveyor belt, etc.). In a preferred embodiment the moving element 50 provides for movement of multiwell vessels in the positive x-direction 95. The tube transport 30 is configured to move the tube array 23 in both the positive and negative y-direction 100, which is substantially perpendicular to the direction of movement provided by the moving element 50. Although the moving element 50 and the tube transport 30 are configured to provide relative movement between the tubes 25 and the vessels 45, other arrangements may be used for providing such relative movement. For example, either a moving element or a tube transport may be individually constructed to provide both x- and y-axis movement.

In a preferred embodiment, tube transport 30 communicates with controller 65 and is moved by electric motors, although other types of transport devices can be employed to move tube transport 30, such as pneumatic, hydraulic, or other suitable devices.

A fluid source 35 comprises a plurality of fluid pumps 37 for pumping fluid to the tubes 25. The fluid pumps 37 are controlled by a plurality of pump control boxes 39, which are typically operated by a controller 65. Although not shown in the figures described herein, fluid pumps 37 are each typically fluidly connected to a separate fluid container or reservoir that contains a particular stock solution, such as those indicated in FIG. 2. The controller 65 may be, for example, a general purpose computing device such as a commonly available PC which has been programmed (as described further below) to perform the steps required by the present invention. The controller 65 is typically operated through an operator interface 70, such as a touch-activated CRT. Other devices can be used to interface with the controller 65, such as a keyboard and mouse, and/or a voice-activated system. Also, controller 65 may be a dedicated controller circuit or processor configured as an embedded controller, and may be locally present or accessed through a network, such as a local or wide area network.

In one embodiment, the fluid pumps 37 are solenoid valve dispensers that are connected to the tubes 25, which are positive displacement syringe pumps. The syringe pumps are configured to dispense very small amounts of fluid. For example, one embodiment of the present invention employs tubes 25 that dispense nanoliters or microliters of fluid, preferably about 1–10 nanoliters or microliters. In a preferred embodiment, the fluid source 35 comprises 96 solenoid valve dispensers each communicating with the 96 tubes 25.

When configured for protein crystallization growth, fluid pumps 37 are each coupled to a fluid source, with each fluid source containing a stock solution that is used to prepare "mother liquors" that are designed to facilitate growth of protein crystals. These stock solutions can be, e.g., salts, buffers, detergents, organic chemicals, and other suitable fluids. Virtually any fluid can be dispensed by the fluid pumps 37 into tubes 25.

Referring to FIGS. 1 and 3, the tube array 23 is arranged to dispense fluid through the tubes 25 into individual wells 40 located in a multi-well plate or vessel 45. The multi-well plates 45 are dispensed from plate dispensers 55 onto a moving element 50. The multi-well plates 45 are carried down the moving element 50, and fluid is dispensed into the wells 40. The plates 45 are optionally collected at the other end of the moving element by plate receivers 60. Alternatively, the plates 45 can be delivered to a diving board 62 for delivery to another device or technician for further processing. Downstream processing is described further below.

Illustrated in FIG. 1, plate dispensers 55 can store a plurality of vessels or plates 45 for dispensing onto moving element 50. The plate dispensers 55 communicate with controller 65 to lower vessels 45 by, for example, a rack-and-pinion unit (not shown). In a similar arrangement, the plate receivers 60 can hold a plurality of plates or vessels 45. The vessels 45 are loaded into plate receivers 60 by an arrangement of posts which can be, for example, rack-and-pinion driven (not shown). Other devices can be used to store and dispense vessels 45. For example, other robotic or manual arrangements may be employed. Robotic grippers are described in greater detail below.

In one embodiment, the present invention can be configured to dispense a multiplicity of different stock solution combinations into a plurality of wells located in vessels 45. In one embodiment, vessel 45 contains a total of 96 wells 40 arranged in eight columns and twelve rows, as illustrated in FIG. 5. The twelve rows are parallel to the y-direction 100 and the columns of vessel 45 are parallel to the x-direction 95. More or fewer wells 40 may be contained in vessel 45.

One particular method of dispensing fluids for growing protein crystals employs four vessels 45, each vessel containing 96 wells 40 for a total of 384 wells. Ninety-six different fluids are dispensed from the 96 tubes 25 mounted on the tube array 23. The combination of tubes 25 and their corresponding stock solutions dispense different combinations and concentrations of stock solutions so that each of the 384 wells contains a unique mixture of fluids. The specific unique mixture in each well is known by the controller and may be used for later process decisions or displayed on the operator interface 70. In this manner, a screen to determine the best combination and concentration of stock solutions for growing an optimum protein crystal can be quickly determined.

In a preferred embodiment, after dispensing the fluids into the 384 wells, protein crystals are grown and selected based on the quality of the crystal according to user-defined criteria. For example, the 16 "best" quality crystals are optionally isolated and the specific combination and concentration of fluids used to grow those crystals are recalled by controller 65 (e.g., from a database component which is described below) and displayed using operator interface 70. Preferably, a "fine-screen" test is performed to optimize the concentration and combination of fluids for each of the 16 fluid combinations that resulted in the 16 best crystals.

During the fine-screen process of this preferred embodiment, 24 variations of each of the 16 fluid combinations are dispensed from the fluid dispensing tubes 25 into new vessel 45 wells 40. For example, if one of the 16 fluid combinations that resulted in a high-quality protein crystal comprised 5 percent of fluid A and 95 percent of fluid B, the corresponding fine screen would be composed of variations of the fluid combination of 5 percent of fluid A and 95 percent of fluid B. As an example, one of the 24 fine screen variations could be composed of 5.1 percent of fluid A and 94.9 percent of fluid B. Other variations could be 5.2 percent of fluid A and 94.8 percent of fluid B or 4.9 percent of fluid A and 95.1 percent of fluid B. In this manner, an optimized fluid combination and concentration can be determined for growing an optimum protein crystal.

III. Software Control System

Overview

The ability to use the fluid dispensing system described herein in an automatic high throughput mode is enhanced by the availability of a higher-level software control system. This control system uses a computer database to determine the activities to be performed and to record the activities that have been performed. This control system preferably has knowledge of the plumbed reagents or stock solutions and their corresponding dispense tips in the machine, have knowledge of the schedule and definition of crystallographic experiments to be performed, the ability to associate and/or assign experiments to specific serialized microtiter plates or other vessels in which the experiments are physically performed, the ability to direct and track movement of the plates in the machine, the ability to interpret and translate the experiments into dispense volumes that are then electronically communicated to the machine, the ability to cause the machine to execute one or more computer programs or methods to carry out movement and positioning of plates using the machine's moving element, move the machine's dispense tips to specific positions over the plates, and dispense the volumes into the plates. The control system also performs other activities to enhance and optimize overall performance and throughput of the machine.

B. Description

The essence of the control system is that it uses a database to direct and record its activities. The database is integral to the operation of the control system and is the repository of all information required to operate the machine in an automated, high throughput fashion.

C. The Machine

The machine is controlled by computer software ("machine software") that is supplied by the machine manufacturer. The machine software executes machine methods. Machine methods allow control of specific, discrete, single unit, independent machine functions, such as index the machine moving element (e.g., a conveyor) to the next position, dispense a specified volume from a specific dispense tip, or move the dispense tips a specified distance across the moving element. Machine methods allow these single unit functions to be combined into a sequence of steps that perform larger units of operations. For some specific machine functions, machine methods allow volume information to be obtained from an electronic file accessible by the machine method.

A person using the machine uses a computer keyboard and mouse to communicate with the machine software. The user can use the machine in manual mode to perform specific, discrete, single unit machine functions, or use the machine software to create and execute machine methods.

To create experiments using the machine software, the user would write a machine method to dispense a specific volume from each dispense tip, then index the dispense tips a specific distance across the plate to the next well, dispense another specific volume from each dispense tip, and so on until all wells in all rows were completed. The machine moving element is designed to accommodate multiple plates concurrently. The user would need to interpret the experiment associated with each plate into the specific dispense volumes from each tip to be dispensed into each well of each plate.

For the use of a typical microtiter plate with 8 columns, the user would enter specific volumes for a total of 768 dispenses (96 tips times 8 columns across the plates) in the machine method. At the conclusion of the machine method, the user would instruct the dispense tips to return to the original position and instruct the moving element to index forward the distance of one well position, and refill the syringes for each dispense tip from their respective fluid containers. The user would then again interpret the experiment associated with each plate then on the moving element and modify the 768 dispense volumes in the machine method accordingly.

A major improvement in this technique would be for the user to use text-editing software to create an electronic file containing the 768 dispense volumes, and modify the machine method to obtain the volumes from this file. As it is much easier for a user to edit a file than to edit a machine method, this is a significant improvement.

Optionally, the machine software can receive electronic communications via a computer network that instruct the machine software to execute machine methods. This process will be referred to as activating a machine method.

D. Control System and Communication with the Machine

The control system is implemented as computer software. The control system communicates with the machine software over a computer network. This communication may take the form of files or electronic messaging protocols. Optionally, the control system could execute on the same computer as the machine software without modifying the means of communication. The control system communicates with the machine software to request execution of machine methods.

E. Database

The database includes the following information:

(1) The list of reagents available for use in experiments that are plumbed into fluid containers attached to the machine and their respective dispense tip assignments. The fluid containers are connected by tubing to the input ports on the machines syringe pumps. The list includes the identities, concentrations, and other characteristics of the reagents, as well as their current volumes in the fluid containers.

(2) The definitions of defined experiment templates ("screens") available to be performed, identifying the specific reagents, final concentrations, and dispense volumes for each plate well.

(3) The identities and other attributes of the protein or other biologic samples that are the objective of the experiments.

(4) The list of actual experiments to be performed, identifying the proteins and screens, as well as the scheduled date/time for the experiment to be performed on the machine. When known, the identifier (e.g., a barcode) of the plate in which each experiment is carried out is also stored.

F. Starting Experiments

Experiments are defined and organized into groups of one or more experiments. When the scheduled date/time for a group of experiments arrives, the group of experiments is eligible to be started. The control system then electronically signals the machine to introduce a new plate (i.e., down stack from the input plate stacker) for the first experiment to be started. The control system then activates a barcode reader attached to the control system computer and reads the barcode of the newly introduced plate. This newly introduced plate is then assigned to the first experiment and records the association of the plate's barcode to the experiment in the database, along with other plate and experiment status information. The control system then records the plate's index position on the moving element in the database. This process is repeated each time there is another experiment to be started when there is room for a new plate on the moving element. A control system option allows for maintaining an inter-plate spacing that enhances throughput under some conditions.

G. Plate Position Tracking

Each time the machine moving element is indexed, the new location for each plate on, entering, or leaving the moving element is updated in the database. The database is updated with plate completion information for plates leaving the moving element.

H. Interpretation of Experiments into Machine Volumes

Each time the control system causes the machine software to execute the machine method to index the machine moving element and thus the plates to the next machine moving element position, the control system analyzes the then current position of plates and their corresponding plate wells in relation to the position of each dispense tip on the moving element. For the first row of plate wells that are aligned with the dispense tips, the control system interprets each well's experiment definition in the database to determine the corresponding volume that is to be dispensed, if any, of the reagent plumbed into (i.e., in fluid communication with) the dispense tip. The process is then repeated for each successive row of wells, and the control system then electronically communicates these dispense volumes to the machine. The control system then electronically communicates with the machine indicating the dispense volumes for each tip for each row of the then-current plates. This communication takes the form of an electronic file that is accessible by the machine software and machine methods. The control system then activates a machine method that dispenses the file-specified volumes for the first row of plate wells, indexes the dispense tips the specified distance to the next row of plate wells, then loops to repeat this process for each row of plate wells.

As a part of the process of interpreting experiments into dispense volumes, several quality control and error checking functions are performed.

If the interpretations of experiments into volumes results in no dispense requirements for the current position of plates on the moving element, the control system reduces the machine cycle time and improves throughput by not activating the dispense machine method but instead activates the moving element index machine method.

An optional alternative approach to the volume file methodology would be to create machine methods for each dispense tip and possible dispense volume. Then, as the experiment for each plate is interpreted, activate the machine methods satisfying the dispense tip and dispense volume experiment interpretation.

I. Reagent Volume Tracking

Each time the machine dispenses a reagent the volume dispensed is subtracted from the current remaining volume for that reagent in its fluid container. If and when the remaining volume falls below a threshold volume in the database associated with that reagent, the control system can issue a warning alert notification by means of a popup message on the control system computer. The warning alert notification can also be displayed on an electronic display board or marquee and can optionally be transmitted electronically to a pager, cell phone, email account, or other electronic, wireless, or printed media.

J. Syringe Volume Tracking and Syringe Refill Optimization

Machine methods normally contain instructions to refill dispense syringes based on a fixed number of dispense cycles of the machine as a whole. The control system can utilize its knowledge of syringe volumetric capacity, track the volume dispensed from each syringe since last refilled, and calculate future dispense volumes for each dispense tip for each next plate index to refill the dispense tip syringes only when necessary or when it will otherwise not impede machine throughput. This optimization can significantly reduce the machine cycle time and increase throughput.

K. Inactivity Timeout Process

The control system can monitor the duration of elapsed time since the last activation of a machine method. When the elapsed time equals or exceeds a threshold, a machine method can be activated to prepare the machine to be idle, performing activities such as cleaning and/or soaking dispense tips.

L. Optional Plate Scheduling Optimization

The control system can analyze the dispense requirements for each plate in the experiment group to determine the most efficient sequence and inter-plate spacing for starting the group of plates, resulting in the shortest total cycle time.

M. Advantages

The control system significantly reduces the time and effort required to operate the machine in a variety of ways. For example, by using the volume file approach, the machine methods can be significantly smaller, containing far fewer lines of instructions, and be reusable without modifications before each use. New experiments can be defined and executed without any changes to the machine software or machine methods. In addition, interpreting experiments into volumes is a tedious and error-prone process even for a single plate. The machine is designed to dispense into multiple plates concurrently, making the process of interpreting experiments significantly more tedious and error prone. By storing experiment definitions electronically and interpreting them into volumes in software, then communicating those volumes to the machine electronically, process is nearly instantaneous without the error-prone characteristics of a manual process. Furthermore, the control system allows automatic assignment of barcodes and plates to experiments.

IV. Parallel Fluid Dispensing Methods

Figure 6:
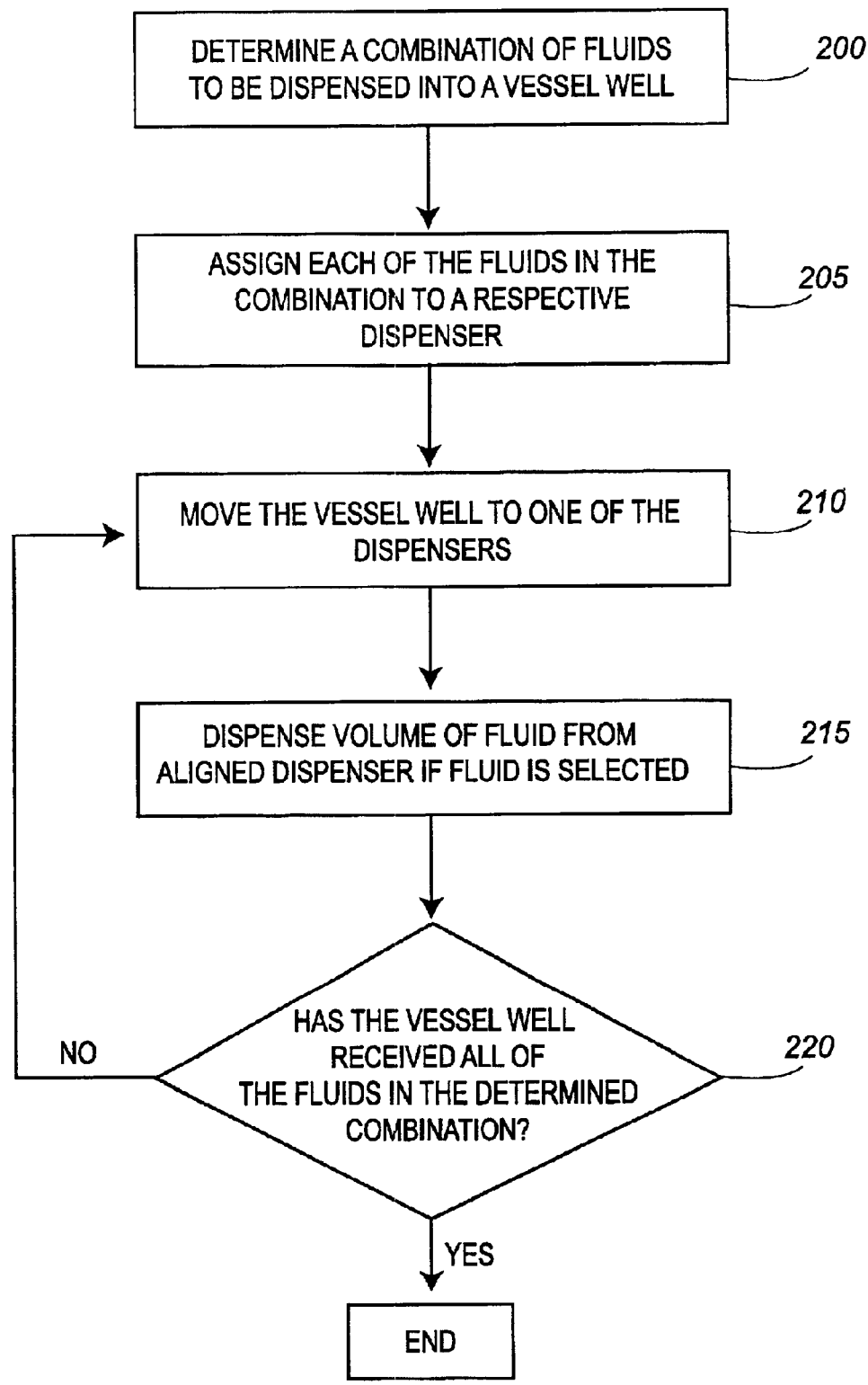
FIG. 6 is a flow chart that illustrates a method of simultaneously producing fluid mixtures in multiple multiwell plates.

Referring to FIGS. 3, 5, and 6, one method for dispensing fluids (e.g., stock solutions, etc.) into vessel 45 wells 40 is described. One embodiment of the present invention can dispense a multiplicity of mother liquor combinations and concentrations for later testing, e.g., for protein crystallization screening. This is useful because a range of fluid combinations and concentrations must be tested to determine which conditions will achieve a suitable protein crystal, since the specific criteria required to achieve a suitable protein crystal has not yet been determined for each protein in, e.g., the human genome.

Referring to FIG. 6, in step 200, a combination of fluids to be dispensed into a vessel 45 well 40 is determined. In step 205, each of the fluids in the combination is assigned to a respective tube. In step 210, the vessel 45 well 40 is moved to one of the tubes. The fluid is then dispensed in a specific amount into the vessel 45 well 40 from the aligned dispenser if that fluid is selected in step 215. Next, step 220 determines whether the vessel has received all of the fluids of the specific fluid combination. If all of the required fluids have been dispensed into the vessel 45 well 40, the process ends. However, if additional fluids must be dispensed into the vessel 45 well 40, then the vessel 45 well 40 is moved to another tube 25, in step 210. Then, step 215 and step 220 are performed as discussed, and this process is repeated until all of the necessary fluids have been dispensed into the specific vessel 45 well 40.

Referring to FIGS. 3 and 6, another procedure for dispensing mother liquors into specific vessel 45 well 40 will be described. Vessels 45 are placed on moving element 50. Each vessel 45 comprises 12 rows 42 and 8 columns 44. Each well 40 and each vessel 45 has a column width of about 9 millimeters and a row width of about 9 millimeters. Other vessels 45 can be employed having different numbers of wells 40 and different well 40 dimensions.

Figure 7:
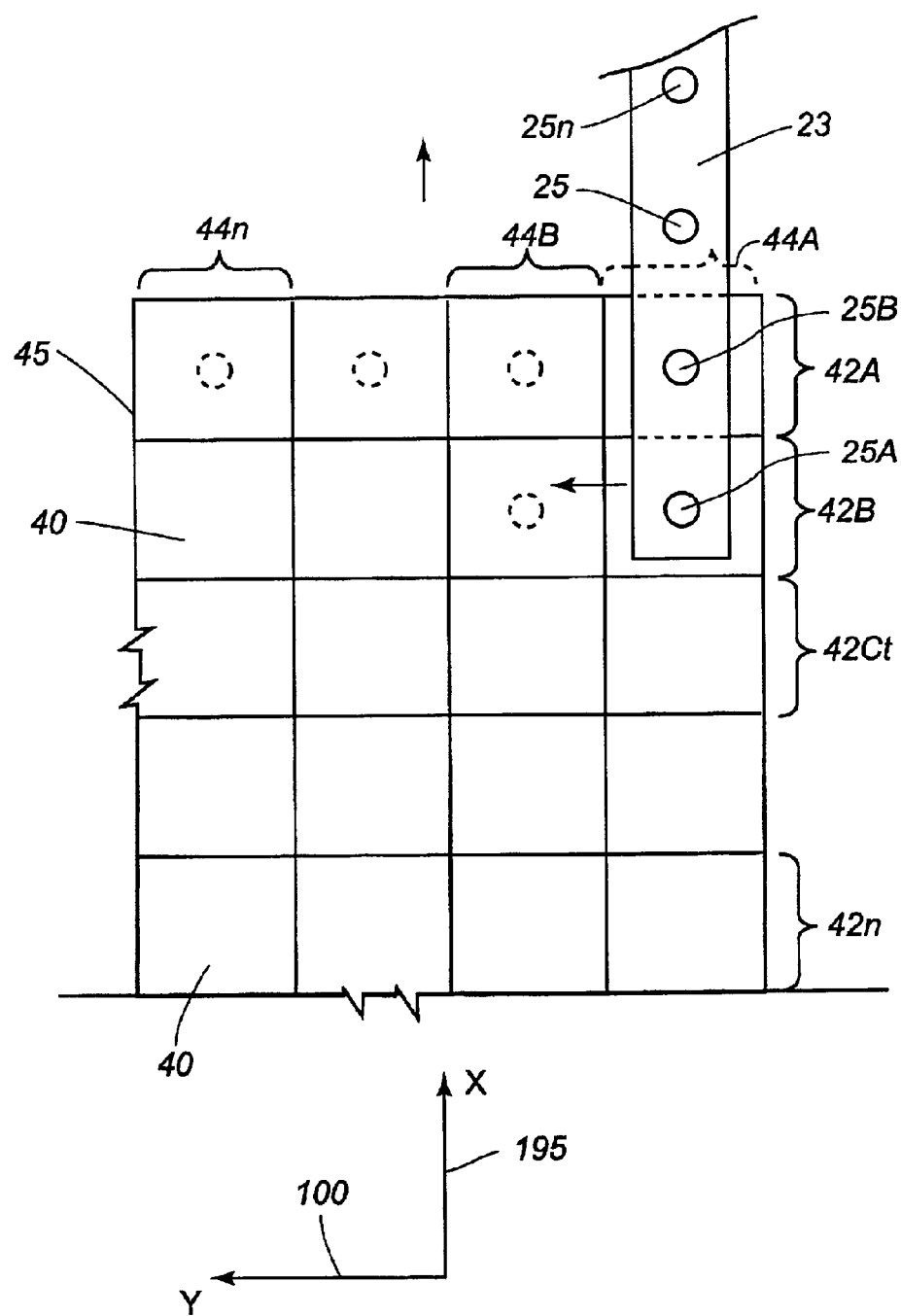
FIG. 7 schematically depicts a segment of a multiwell plate disposed below a segment of a support structure that includes linearly arrayed dispense tips.

After the vessel 45 is placed on the moving element 50, the moving element moves the vessel 45 in 9 millimeter increments in the x-direction 95. Tube array 23 containing 96 tubes 25 is moved by tube transport 30 in the y-direction 100. As illustrated in FIG. 7, controller 65 aligns the first tube 25A of the tube array 23 over a first well 40 in a first row 42A, first column 44A. As discussed above and illustrated in FIG. 6, the controller determines whether or not a fluid must be dispensed into that specific vessel 45 well 40. If the controller orders fluid to be dispensed into that specific well 40, the fluid is dispensed through the first tube 25A.

The tube array 23 is then moved by tube transport 30 over one column (i.e., 9 millimeters). This positions the first tube 25A over a second well 40 in the first row 42A, second column 44B. Again, controller 65 determines whether or not fluid is to be dispensed into the second well 40. Once the fluid has been dispensed, if necessary, the tube transport 30 moves the tube array 23 a distance of 9 millimeters to the next column 44C and positions the first tube 25A over a third well 40. This process is repeated until the first tube 25A has been positioned over each well 40 in the first row 42A of the plate 45. Moving element 50 then moves the plate 45 in the x-direction 95 9 millimeters, positioning the first tube 25A over the first well in the second row 42B.

As illustrated in FIG. 7, first tube 25A coupled to tube array 23 and second tube 25B also coupled to tube array 23 are positioned over the first well 40 of the first two rows 42A and 42B. The procedure described in step 210 of FIG. 6 is now repeated for the first well 40 in row 42B as well as the first well of row 42A. Because two tubes 25A and 25B are positioned over two wells 40, two different fluids can be dispensed simultaneously, if necessary, depending upon the combination of fluids to be dispensed into each well 40. Once the controller has determined if a fluid is to be dispensed into each well and that dispensing has occurred, the tube transport 30 moves the tube array 23 in the y-direction 100 to position the first tube 25A and second tube 25B over the next column 44B in the plate 45. The dispensing of fluids then commences, if selected, for that well 40. In this manner, appropriate fluids can be dispensed in selected combinations and concentrations into each well 40 of each vessel 45.

Referring again to FIGS. 3 and 5, as the vessels 45 progress down the moving element 50 and are exposed to more tubes 25 and the tube array 23, the controller can dispense up to 96 fluids substantially simultaneously, if necessary. In this manner, an extremely high throughput production of fluid combinations can be achieved in the wells 40 of each vessel 45. The rate of fluids that can be dispensed by the present invention is unachievable by human technicians and allows any for an extremely high number of combinations of fluids to be dispensed. In addition, each combination and concentration of fluids in each well 40 can be recalled from the operator interface 70, and can be reproduced with high accuracy due to the automated process performed by the present invention.

The arrangement of tubes need not be in a linear arrangement as illustrated in FIG. 3. For example, as shown in FIG. 5, the tubes 25 can be arranged in a staggered configuration or any other suitable configuration.

Referring further to FIG. 5, the tubes 25 can be periodically cleaned, e.g., rinsed and dried so that the concentrations of fluids dispensed through the tubes remain consistent. Tube transport 30 positions the tube array 23 over the tube bath 80 that contains a suitable rinsing fluid, such as ethanol, deionized water, or the like. For example, the tubes are optionally immersed in the rinse and then moved by the tube transport 30 to the tube dryer 85 that is connected to a vacuum source 90. The tube dryer 85 includes tube holes 87 into which the tubes 25 are inserted by the tube transport 30. The vacuum source 90 is turned on by the controller 65 to effect tube drying.

Once a multiwell plate has been processed (i.e., the desired fluid mixtures have been produced in selected wells of the multiwell plate), the plate can be agitated to facilitate mixing of the fluids. The agitation can be accomplished using a robot, for example.

V. Associated Systems and Processes

The massively parallel fluid dispensing systems and related methods described herein for simultaneously producing multiple mother liquors in multiple multiwell plates are typically utilized as components of high throughput crystallization processes. Associated systems and methods used in this integrated high throughput approach include fermenting a plurality of samples, which typically includes providing a plurality of sample vessels each holding a fermentation sample in a sample carrier, fermenting the fermentation samples in the plurality of sample vessels in the carrier, and transporting the samples once fermented to a processing station where the samples may be further processed. Additional details relating to methods, devices and systems for fermentation are described in, e.g., U.S. patent application entitled "Multi-Sample Fermentor and Method of Using Same" Ser. No. 09/780,591, filed Feb. 8, 2001, and in U.S. patent application entitled "MultiSample Fermentor and Method of Using Same," Ser. No. 10/071, 842, filed Feb. 8, 2002. Further processing may include, for example, centrifugation, sonication, and/or protein purification, which are described in, e.g., U.S. patent r; application entitled "Automated Centrifuge and Method Of Using Same," Ser. No. 09/780,589, filed Feb. 8, 2001, and in international patent application entitled "Automated Centrifuge and Method Of Using Same," PCT/W02/03822, filed Feb. 8, 2002. Samples and/or fluid mixtures in a vessel or plate may be moved, for example, from a fermentor to a centrifuge, from a fluid dispensing system to another processing station by a robotic gripper as described in, e.g., U.S. patent application entitled "Gripper Mechanism," Ser. No. 09/793,254, filed Feb. 26, 2001, and in international patent application entitled "Gripping Mechanisms, Apparatus, and Methods," PCT/US02/06096, filed Feb. 26, 2002. Additional details regarding the fermentation, centrifugation, purification, and robotic grippers used to prepare protein samples for crystallization screens are also described in, e.g., international patent application entitled "METHOD AND APPARATUS FOR PERFORMING MULTIPLE PROCESSING STEPS ON A SAMPLE IN A SINGLE VESSEL," PCT/US02/08384, filed Mar. 18, 2002.

To further illustrate the invention, the fluid dispensing systems described herein typically include, e.g., a gripper apparatus that translocates the multiwell plates between the massively parallel fluid dispensing system and other systems, which are also optionally included. For example, some of these other systems include one or more of a fluid aspiration/dispense system that aspirates fluids from the wells of the multiwell plates and dispenses fluids into the wells of the multiwell plates, a test sample dispense system that dispenses aliquots of test samples (e.g., polypeptide samples, etc.) into the wells of the multiwell plates, a multiwell plate sealing system that seals the wells of the multiwell plates (described further below), or the like. Certain of these other systems, or components thereof, are commercially available from sources, such as Cartesian Technologies, Inc. (Irvine, Calif.).

It is particularly important to seal microcrystallizations shortly after forming crystallization solutions, e.g., to prevent volatile fluid components of mother liquor solutions from evaporating. Such evaporation can materially alter the composition of the crystallization solution. Preferably, microcrystallizations are sealed within one minute, more preferably within 30 seconds, even more preferably within 15 seconds, and most preferably within 5 seconds of forming the microcrystallization. One difficulty arises in sealing all of the crystallizations in a particular array rapidly. There are many microcrystallizations in a given plate, typically at least 96. In addition, the microcrystallizations are prepared at different stations. According to the present invention, recognizing that one needs to seal the microcrystallization fast, a robot is provided which grips a plate, moves it to a first station where protein and mother liquor drops are deposited, and then moves the microcrystallizations to another station where the plate is sealed. In some embodiments, this is all done without the robot letting go of the plate. This is because the time required to position a plate at the first station, let go of the plate, have the robot pick up the plate, and position the plate at the next station is often too long. Protein crystallization plates are typically sealed with cellophane, lids, or other sealing methods, which establish substantially hermetic seals.

In preferred embodiments, multiwell plates utilized are protein crystallization plates in which each well includes a reagent reservoir and a crystallization platform (e.g., a microbridge or the like) elevated above the reagent fluid container. In these embodiments, the methods typically further include (d) aspirating a fluid mixture from a reagent reservoir in a selected well of a processed multiwell plate with an aspiration/dispense system, (e) dispensing an aliquot of a test sample (e.g., a polypeptide or other macromolecule to be crystallized) onto the crystallization platform of the selected well with a sample dispensing system, and (f) dispensing selected volumes of the aspirated fluid mixture of (d) onto the crystallization platform with the aspiration/dispense system in which the dispensed fluid mixture is placed in contact with the aliquot of the test sample. These embodiments also include (g) repeating (d) through (f) for additional test samples, if any, and (h) sealing the wells of the processed multiwell plate with a multiwell plate sealing system. In addition, the processed multiwell plate is typically gripped and translocated between the massively parallel fluid dispensing system, the aspiration/dispense system, the test sample dispensing device system, and the multiwell plate sealing system with a gripper apparatus (described above). In these embodiments, (d) through (h) are typically completed without having the gripper apparatus release the multiwell plate, which further increases the throughput of the overall process, increases the positional accuracy of plate location, and minimizes evaporation, as described above. Typically, (d) through (h) are completed in one minute or less for each processed plate.

The fluid mixtures produced in these embodiments generally include crystallization mother liquor solutions and the test samples include molecules (e.g., polypeptides or other macromolecules) to be crystallized. Accordingly, these embodiments generally also include (i) storing the processed multiwell plate of (h) under conditions suitable for test sample crystals to form in the wells, and (j) detecting the test sample crystals formed in the wells. A total combined volume of the test samples and the crystallization mother liquor solutions dispensed on the crystallization platform is typically less than 10 $\mu$l, more typically less than 1 $\mu$l, and still more typically less than 750 nl (e.g., less than 500 nl, less than 250 nl, or between about 1 nl and about 250 nl).

Figure 8:
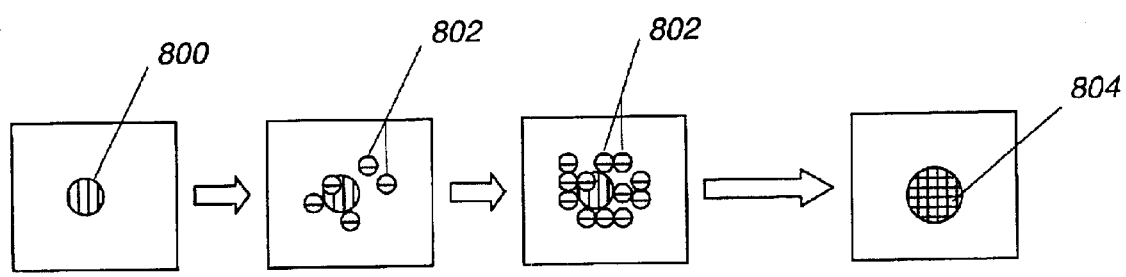
FIG. 8 schematically shows a method of mixing multiple subvolumes of a mother liquor solution with a protein solution.

In another aspect, this invention relates to the realization that surface tension between mother liquor and protein solutions interferes with the two solutions mixing. As a result, further steps are typically needed in order to get the protein and mother liquor to mix. Specifically, one generally first delivers the protein solution and then delivers the mother liquor solution. Rather than delivering the mother liquor solution in a single volume, the mother liquor solution is optionally delivered as a series of smaller volumes. The series of smaller volumes are preferably spread around the region where the mixture is being formed. This is schematically illustrated in FIG. 8, which shows multiple subvolumes 802 being added to protein solution 800 to form mixture 804 following agitation. Accordingly, in certain embodiments, (f) includes dispensing the selected volume of the crystallization mother liquor solution as a plurality of separate subvolumes (e.g., as between about two and about 10 separate subvolumes) that are placed in contact with the test sample on the crystallization platform. In these embodiments, the methods typically further include agitating the processed multiwell plate of (f) after at least one set of the separate subvolumes is dispensed such that the test samples and the crystallization mother liquor solutions admix with each other.

One skilled in the art will appreciate that the present invention can be practiced by other than the preferred embodiments which are presented in this description for purposes of illustration and not of limitation, and the present invention is limited only by the claims that follow. For example, features of the methods and devices described in International Patent Publication WO 00/78445, published Dec. 28, 2000 and in U.S. Pat. No. 6,296,673, entitled "METHODS AND APPARATUS FOR PERFORMING ARRAY MICROCRYSTALLIZATIONS," issued Oct. 2, 2001 to Santarsiero et al., which are incorporated herein by reference in their entirety including any drawings or figures, can be used in conjunction with the methods and devices of the present invention. It is noted that equivalents for the particular embodiments discussed in this description may practice the invention as well.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A fluid dispensing system that comprises at least one linear array of fluid dispensers, wherein each fluid dispenser corresponds to a single well of a multiwell plate and the linear array comprises:
   a number of fluid dispensers that is greater than the number of wells in a line of wells of a single multiwell plate, wherein the line of wells is parallel to a longitudinal axis of the linear array; and,
   at least two fluid dispensers that are spaced at least a sufficient distance apart to simultaneously dispense a fluid into a well of a first multiwell plate and a corresponding well of a second multiwell plate when both plates are placed beneath the linear array of fluid dispensers.

2. The fluid dispensing system of claim 1, wherein each fluid dispenser separately dispenses selected volumes between 1 nl and 500 ml.

3. The fluid dispensing system of claim 1, wherein each of the multiwell plates comprises 6, 12, 24, 48, 96, 384, 1536, or more wells.

4. The fluid dispensing system of claim 1, wherein:
   the number of fluid dispensers in the linear array is at least as great as the number of wells in two lines of wells of a single multiwell plate; and
   the fluid dispensers are spaced an appropriate distance apart from one another to simultaneously dispense a fluid into wells of multiple multiwell plates when the plates are placed underneath the fluid dispensers.

5. The fluid dispensing system of claim 1, comprising a plurality of linear arrays, each of which comprises at least two fluid dispensers that are spaced at least a sufficient distance apart to simultaneously dispense a fluid into a well of a first multiwell plate and a corresponding well of a second multiwell plate when both plates are placed beneath the array of fluid dispensers.

6. The fluid dispensing system of claim 1, wherein the line of wells of the multiwell plate is a row of wells.

7. The fluid dispensing system of claim 1, wherein the line of wells of the multiwell plate is a column of wells.

8. The fluid dispensing system of claim 1, wherein adjacent dispensers are spaced 144 mm, 72 mm, 36 mm, 18 mm, 9 nm, 4.5 mm, 2.25 mm or less apart from one another.

9. The fluid dispensing system of claim 1, wherein adjacent dispensers are spaced an appropriate distance apart to allow the adjacent fluid dispensers to simultaneously dispense a fluid into adjacent wells of a 96-well plate.

10. The fluid dispensing system of claim 1, wherein the line of wells includes eight wells and the linear array comprises at least nine fluid dispensers.

11. The fluid dispensing system of claim 1, wherein the line of wells includes twelve wells and the linear array comprises at least thirteen fluid dispensers.

12. The fluid dispensing system of claim 1, wherein the linear array comprises 96 fluid dispensers.

13. The fluid dispensing system of claim 1, wherein the linear array comprises at least 17 fluid dispensers.

14. The fluid dispensing system of claim 13, wherein the linear array comprises at least 25 fluid dispensers.

15. The fluid dispensing system of claim 14, wherein the linear array comprises at least 33 fluid dispensers.

16. The fluid dispensing system of claim 1, wherein the number of fluid dispenser is x times the number of wells in the line of wells of a single multiwell plate and x is a whole number greater than or equal to 2.

17. The fluid dispensing system of claim 16, wherein x is selected from the group consisting of: 2, 3, 4, 5, 6, 7, 8, 9, and 10.

18. The fluid dispensing system of claim 1, wherein each of the fluid dispensers comprises a solenoid valve or a piezoelectric valve.

19. The fluid dispensing system of claim 1, further comprising one or more cleaning devices to clean the fluid dispensers.

20. The fluid dispensing system of claim 1, wherein at least a first fluid dispenser in the linear array is connected to a fluid container that contains a first fluid and at least a second fluid dispenser in the linear array is connected to a fluid container that contains a second fluid that differs from the first fluid.

21. The fluid dispensing system of claim 20, wherein adjacent fluid dispensers dispense different fluids.

22. The fluid dispensing system of claim 20, wherein the first and second fluids are independently selected from the group consisting of: water, a stock solution, a buffer, a reagent, a solvent, a salt solution, a polymer solution, an inorganic solution, an organic solvent, and a cell suspension.

23. The fluid dispensing system of claim 22, wherein:
   at least a first fluid dispenser in the linear array is connected to a fluid container that contains water;
   at least a second fluid dispenser in the linear array is connected to a fluid container that contains a salt solution;
   at least a third fluid dispenser in the linear array is connected to a fluid container that contains a polymer solution; and
   at least a fourth fluid dispenser in the linear array is connected to a fluid container that contains an organic solvent.

24. The fluid dispensing system of claim 23, wherein:
   the salt solution comprises one or more components selected from the group consisting of cacodylic acid, CHES, HEPES, citric acid, malonic acid, MES, phosphoric acid, acetic acid, and a salt thereof;
   the polymer solution comprises one or more components selected from the group consisting of glycerol, ethylene glycol, formate, spermine, and polyethylene glycol; and
   the organic solvent comprises one or more components selected from the group consisting of 1,2-propanediol, DMSO, methanol, dioxane, trifluoroethanol, MPD, ethanol, and isopropanol.

25. The fluid dispensing system of claim 24, wherein each of the components is contained in at least one fluid container which is connected to a fluid dispenser in the linear array.

26. The fluid dispensing system of claim 1, wherein the linear array of fluid dispensers is configured so that the fluid dispensers can deliver fluid to at least three multi-well plates at the same time.

27. The fluid dispensing system of claim 26, wherein the linear array of fluid dispensers is configured so that the fluid dispensers can deliver fluid to at least four multi-well plates at the same time.

28. The fluid dispensing system of claim 1, wherein at least one of the fluid dispensers comprises:
(i) at least one fluid conduit in fluid communication with a fluid source; and
(ii) at least one pump operably connected to the fluid conduit to convey fluid through the fluid conduit from the fluid source to the wells of the multiwell plates.

29. The fluid dispensing system of claim 28, wherein the fluid conduit composes a flexible tube.

30. The fluid dispensing system of claim 28, wherein the pump comprises a peristaltic pump or a syringe pump.

31. The fluid dispensing system of claim 1, further comprising a moving element that moves the multiwell plates in a direction parallel to a longitudinal axis of the linear array of fluid dispensers.

32. The fluid dispensing system of claim 31, wherein the moving element comprises a conveyor belt.

33. The fluid dispensing system of claim 31, wherein the moving element has a length of at least n of the multiwell plates, wherein n is the number of the multiwell plates.

34. The fluid dispensing system of claim 33, wherein n is a whole number selected from the group consisting of 2, 3, 4, 5, 6, 7, 8, 9, and 10.

35. The fluid dispensing system of claim 31, wherein the linear array of fluid dispensers comprises a support structure that is operably connected to a drive mechanism that reversibly moves the support structure in a direction perpendicular to a direction of movement of the moving element.

36. The fluid dispensing system of claim 35, further comprising a controller that is operably connected to the fluid dispensers, the moving element, and the drive mechanism, which controller controls at least fluid dispensation from the fluid dispensers, moving element movement, and support structure movement.

37. The fluid dispensing system of claim 1, wherein the system comprises system control logic which directs when fluid is dispensed from a given fluid dispenser to a well of a mutiwell plate based on a position of the multiwell plate in the system.

38. The fluid dispensing system of claim 1, further comprising one or more of:
a gripper apparatus that translocates the multiwell plates between the fluid dispensing system and other systems;
a fluid aspiration/dispense system that aspirates fluids from the wells of the multiwell plates and dispenses fluids into the wells of the multiwell plates;
a test sample dispense system that dispenses aliquots of test samples into the wells of the multiwell plates; and
a multiwell plate sealing system that seals the wells of the multiwell plates.

39. The fluid dispensing system of claim 38, wherein the test samples comprise polypeptide samples.

40. The fluid dispensing system of claim 36, wherein the controller comprises at least one logic device and at least one database.

41. The fluid dispensing system of claim 40, wherein the logic device comprises one or more logic instructions that direct the fluid dispensing system to:
move the moving element a selected distance;
move the support structure a selected distance; and
dispense selected volumes of fluids from selected fluid dispensers into selected wells of the multiwell plates.

42. The fluid dispensing system of claim 41, wherein the logic instructions direct the fluid dispensing system to:
(a) sequentially position each well of two or more multiwell plates underneath each of the fluid dispensers; and
(b) dispense selected volumes of fluid from selected fluid dispensers into selected wells of the multiwell plates when the selected fluid dispensers are positioned above the selected wells, thereby simultaneously producing multiple fluid mixtures in two or more multiwell plates.

43. The fluid dispensing system of claim 41, wherein the logic instructions direct the fluid dispensing system to:
position a first well of a first row of a multiwell plate under a first fluid dispenser;
move the support structure sequentially across the entire first row of a multiwell plate, dispensing selected volumes of a first fluid from the first fluid dispenser into one or more selected wells in the first row when the fit fluid dispenser is positioned above the selected well;
sequentially advance the moving element to position a first well of a second row of a multiwell plate under the first fluid dispenser and the first well of the first row under a second fluid dispenser, and
move the support structure sequentially across the entire first and second rows, dispensing selected volumes of a first fluid from the first fluid dispenser into one or more selected wells in the second row when the first fluid dispenser is positioned above the selected well, and dispensing selected volumes of a second fluid from the second fluid dispenser into one or more selected wells in the fist row when the second fluid dispenser is positioned above the selected well.

44. The fluid dispensing system of claim 41, wherein the database comprises information about:
fluids in fluid containers that are in fluid communication with the fluid dispensers;
selected wells into which a selected fluid dispenser is to dispense a selected fluid, wherein the selected wells are located on two or more multiwell plates; and
selected volumes of the selected fluids that are to be dispensed into each selected well.

45. A method of simultaneously producing multiple fluid mixtures in multiple multiwell plates, the method comprising:
(a) providing a fluid dispensing system that comprises an at least one linear array of fluid dispensers, wherein each fluid dispenser corresponds to a single well of a multiwell plate and the linear array comprises:
a number of fluid dispenser that is greater than the number of wells in a line of wells of a single multiwell plate, wherein the line of wells is parallel to a longitudinal is of the linear array; and,
at least two fluid dispensers that are spaced at least a sufficient distance apart to simultaneously dispense a fluid into a well of a fist multiwell plate and a corresponding well of a second multiwell plate when both plates are placed beneath the linear array of fluid dispensers;
(b) sequentially positioning each well of the multiple multiwell plates underneath each of the fluid dispensers; and
(c) dispensing selected volumes of fluid from selected fluid dispensers into selected wells of the multiple multiwell plates when the selected fluid dispensers are positioned above the selected wells, thereby simultaneously producing the multiple fluid mixtures in multiple multiwell plates.

46. The method of claim 45, wherein at least a first fluid dispenser in the linear array is connected to a fluid container that contains a fiat fluid, and at least a second fluid dispenser in the linear array is connected to at least a second fluid container that contains at least a second fluid that differs from the first fluid.

47. The method of claim 46, wherein at least two different fluids are dispensed into each selected well of the multiwell plates.

48. The method of claim 46, wherein each fluid container holds a stock solution and each selected well receives fluid from a plurality of fluid containers.

49. The method of claim 46, wherein the first and second fluids are independently selected from the group consisting of: water, a stock solution, a buffer, a reagent, a solvent, a salt solution, a polymer solution, an inorganic solution, an organic solvent, and a cell suspension.

50. The method of claim 49, wherein:
    at least a first fluid dispenser in the linear array is connected to a fluid container that contains water;
    at least a second fluid dispenser in the linear array is connected to a fluid container that contains a salt solution;
    at least a third fluid dispenser in the linear array is connected to a fluid container that contains a polymer solution; and
    at least a fourth fluid dispenser in the linear array is connected to a fluid container that contains an organic solvent.

51. The method of claim 50, wherein:
    the salt solution comprises one or more components selected from the group consisting of cacodylic acid, CHES, HEPES, citric acid, malonic acid, MES, phosphoric acid, acetic acid, and a salt thereof;
    the polymer solution comprises one or more components selected from the group consisting of glycerol, ethylene glycol, formate, spermine, and polyethylene glycol; and
    the organic solvent comprises one or more components selected from the group consisting of 1,2-propanediol, DMSO, methanol, dioxane, trifluoroethanol, MPD, ethanol, and isopropanol.

52. The method of claim 45, wherein the fluid dispensing system comprises a plurality of linear arrays, each of which comprises at least two fluid dispensers that are spaced at least a sufficient distance apart to simultaneously dispense a fluid into a well of a first multiwell plate and a corresponding well of a second multiwell plate when both plates are placed beneath the linear away of fluid dispensers.

53. The method of claim 45, wherein the line of wells of the multiwell plate is a row of wells.

54. The method of claim 45, wherein the line of wells of the multiwell plate is a column of wells.

55. The method of claim 45, wherein the number of fluid dispensers is x times the number of wells in the line of wells of the multiwell plate and x is a whole number greater than or equal to 2.

56. The method of claim 55, wherein x is selected from the group consisting of: 3, 4, 5, 6, 7, 8, 9, and 10.

57. The method of claim 45, wherein each of the multiwell plates comprises 6, 12, 24, 48, 96, 384, 1536, or more wells.

58. The method of claim 45, wherein the selected volumes comprise between about 1 nl and about 500 ml.

59. The method of claim 45, wherein one or more of the fluid mixtures comprise 2, 3, 4, 5, 6, 7, 8, 9, 10, or more mixed fluids.

60. The method of claim 45, further comprising cleaning the fluid dispensers after one or more of the selected volumes are dispensed.

61. The method of claim 45, wherein the multiwell plates are protein crystallization plates in which each well comprises a reagent fluid container and a crystallization platform elevated above the reagent reservoir.

62. The method of claim 61, wherein the crystallization platform is a micro-bridge.

63. The method of claim 61, further comprising:
    (d) aspirating a fluid mixture from a reagent reservoir in a well of a processed multiwell plate with an aspiration/dispense system;
    (e) dispensing an aliquot of a test sample onto the crystallization platform of the selected well with a sample dispensing system;
    (f) dispensing selected volumes of the aspirated fluid mixture of (d) onto the crystallization platform with the aspiration/dispense system, wherein the dispensed fluid mixture is placed in contact with the aliquot of the test sample;
    (g) repeating (d) through (f) for additional test samples, if any, and
    (h) sealing the wells of the processed multiwell plate with a multiwell plate sealing system.

64. The method of claim 63, wherein the processed multiwell plate is gripped and translocated between the fluid dispensing system, the aspiration/dispense system, the test sample dispensing device system, and the multiwell plate sealing system with a gripper apparatus.

65. The method of claim 64, wherein (d) through (h) are completed without having the gripper apparatus release the multiwell plate.

66. The method of claim 64, wherein (d) through (h) are completed in one minute or less.

67. The method of clam 63, wherein the fluid mixtures comprise crystallization mother liquor solutions and the test samples comprise molecules to be crystallized.

68. The method of claim 67, further comprising:
    (i) storing the processed multiwell plate of (h) under conditions suitable for test sample crystals to form in the wells; and
    (j) detecting the test sample crystals formed in the wells.

69. The method of claim 67, wherein the molecules comprise macromolecules.

70. The method of claim 69, wherein the test samples further comprise a molecule that can form a complex with the macromolecule.

71. The method of claim 67, wherein the molecules comprise polypeptides.

72. The method of claim 67, wherein a total combined volume of the test sample and the crystallization mother liquor solution dispensed on the crystallization platform in the selected well is less than 10 ml.

73. The method of claim 72, wherein the total combined volume of the test sample and the crystallization mother liquor solution dispensed on the crystallization platform is less than 1 ml.

74. The method of claim 73, wherein the total combined volume of the test sample and the crystallization mother liquor solution dispensed on the crystallization platform is less than 750 nl.

75. The method of claim 74, wherein the total combined volume of the test sample and the crystallization mother liquor solution dispensed on the crystallization platform is less than 500 nl.

76. The method of claim 75, wherein the total combined volume of the test sample and the crystallization mother liquor solution dispensed on the crystallization platform is less than 250 nl.

77. The method of claim 75, wherein the total combined volume of the test sample and the crystallization mother liquor solution dispensed on the crystallization platform is between 1 nl and 250 nl.

78. The method of claim 67, wherein (f) comprises dispensing the selected volume of the crystallization mother liquor solution as a plurality of separate subvolumes that are placed in contact with the test sample on the crystallization platform.

79. The method of claim 78, further comprising agitating the processed multiwell plate of (f) after at least one set of the separate subvolumes is dispensed such that the test samples and the crystallization mother liquor solutions admix with each other.

80. The method of claim 78, wherein the selected volumes are dispensed as between about two and about 10 separate subvolumes.

81. An apparatus for preparing fluid mixtures in a plurality of multi-well vessels, each of the multiwell vessels having a plurality of wells, the apparatus comprising:
   a multi-well vessel moving apparatus configured to receive and move the plurality of multi-well vessels in a first direction;
   a plurality of tubes, each tube configured to dispense a fluid into individual wells of the multi-well vessels, where the tubes have a footprint in the column direction, where each of the multi-well vessels has a footprint in the column direction, where the footprint of the tubes in the column direction is longer than the footprint of any single one of the multi-well vessels in the column direction;
   a tube mover configured to move the plurality of tubes in a second direction; and
   a controller communicating with the vessel moving apparatus, the plurality of tubes and the tube mover, the controller programmed to selectively move the multi-well vessels and the tube mover and dispense fluid into individual wells of the multi-well vessels.

82. An apparatus for preparing fluid mixtures, comprising:
   a vessel receiving area constructed to hold a plurality of multi-well vessels, with each vessel configured to hold a fluid mixture;
   a plurality of dispensers, each dispenser configured to dispense a determined quantity of a fluid into one well of the multi-well vessels; where the dispensers have a footprint in the column direction, where each of the multi-well vessels has a footprint in the column direction, where the footprint of the dispensers in the column direction is longer than the footprint of any single one of the multi-well vessels in the column direction;
   a mover configured to position a selected one of the dispensers directly above a selected one of the wells of the multi-well vessels; and
   a controller communicating with the mover and the dispensers, the controller configured to control the positioning of the mover and to control the dispensing of the fluid.

83. A system for preparing mother liquors in multi-well sample plates for a protein crystallization screen, the mother liquor being a mixture of stock liquids, the system comprising:
   a plurality of fluid dispensers arranged in an array, at least two of the fluid dispensers dispensing different stock liquids, where the fluid dispensers have a footprint in the column direction, where each of the multi-well vessels has a footprint in the column direction, where the footprint of the fluid dispensers in the column direction is longer than the footprint of any single one of the multi-well vessels in the column direction;
   a drive mechanism constructed to position fluid dispensers in the array directly over wells in the sample plates, the sample plates having sample wells arranged in rows and columns; and
   a processor performing the steps of:
      receiving instruction on the formulation of each mother liquor in each sample well, the formulation being a combination of the stock liquids;
      calculating the quantity of each stock liquid to be dispensed into each sample well;
      moving the fluid dispenser array to a new row position;
      directing the drive mechanism to position the fluid dispenser array directly above a new column of sample wells;
      identifying which positioned fluid dispensers have a stock liquid required for the formulation in the sample well associated with each positioned fluid dispenser;
      dispensing, with the identified fluid dispensers, the calculated quantity of stock liquid into each respective sample well; and
      repeating the moving, directing, identifying, and dispensing steps until all instructed formulations are complete.

84. A system for efficiently preparing mother liquors in a plurality of multi-well sample plates for a protein crystallization screen, the plurality of sample plates arranged with corresponding columns aligned, the system comprising:
   a plate arranging area configured to receive the plurality of sample plates;
   a plurality of fluid containers, each fluid container holding a stock solution;
   a plurality of fluid dispensers arranged in an array, each fluid dispenser being in fluid communication with an associated one of the fluid containers, where the fluid dispensers have a footprint in the column direction, where each of the multi-well vessels has a footprint in the column direction, where the footprint of the fluid dispensers in the column direction is longer than the footprint of each of the multi-well vessels in the column direction;
   a drive mechanism constructed to sequentially position the fluid dispensers in the array directly over each column of wells in the sample plates;
   a dispensing mechanism associated with each fluid dispenser; and
   a fluid controller communicating with the dispensing mechanism;
   wherein the fluid controller directs the dispensing mechanisms to deliver a quantity of each associated stock solution into each sample well in a column before the drive mechanism moves the fluid dispenser array to a next column.

85. The system of claim 84, wherein the plurality of fluid dispensers are configured so that at least two sample plates can be beneath the plurality of fluid dispensers at the same time.

86. The system of claim 84, wherein the plurality of fluid dispensers are configured so that at least three sample plates can be beneath the plurality of fluid dispensers at the same time.

87. The system of claim 84, wherein the plurality of fluid dispensers are configured so that at least four sample plates can be beneath the plurality of fluid dispensers at the same time.

88. The system of claim 84, wherein the plurality of fluid dispensers are configured so that the dispensing mechanisms can deliver the material to at least two sample plates at the same time.

89. The system of claim 84, wherein the plurality of fluid dispensers are configured so that the dispensing mechanisms can deliver the material to at least three sample plates at the same time.

90. The system of claim 84, wherein the plurality of fluid dispensers are configured so that the dispensing mechanisms can deliver the material to at least four sample plates at the same time.

91. The system of claim 84, wherein the plurality of fluid dispensers are configured so that all of the dispensing mechanisms can deliver the material at the same time.

92. The system of claim 84, wherein the system includes a moving element that has a length of at least n of the sample plates, wherein n is the number of the sample plates, wherein each of the sample plates has m wells, wherein m is the number of wells, wherein the system processes one of the sample plates every m dispensings even though each of the sample plates is in the system for n times m dispensings.

93. The system of claim 92, wherein the moving element has a length of at least two sample plates, wherein each sample plate has 96 wells.

94. The system of claim 92, wherein the moving element has a length of at least three sample plates, wherein each sample plate has 96 wells.

95. The system of claim 92, wherein the moving element has a length of at least four sample plates, wherein each sample plate has 96 wells.

96. The system of claim 84, the fluid controller directs the delivery of the material from each fluid container to each of the sample plates.

97. The system of claim 96, wherein the dispenser controller directs the delivery of the material from each of at least eight fluid containers to each of at least two multi-well plates.

98. A method for automatically preparing a mixture in a well of a multi-well holder, said method comprising the steps of:
moving the multi-well holder so that at least one of the wells is positioned below a fluid dispensing device of an array of fluid dispensing devices, where each fluid dispensing device is configured to dispense fluid into individual wells of the multi-well holder, where the array of fluid dispensing devices has a footprint in the column direction, where each of a plurality of multi-well holders has a footprint in the column direction, where the footprint of the array of fluid dispensing devices in the column direction is longer than the footprint of any single one of the multi-well holders in the column direction;
dispensing the fluid from the fluid dispensing device into the well; and
repeatedly moving the multi-well holder so that the well is positioned below a next fluid dispensing device of the array of fluid dispensing devices and dispensing fluid from the next fluid dispensing device into the well until a predetermined mixture is prepared in the well.

99. A method of preparing mother liquors in multi-well sample plates, each of the multi-well sample plates having an array of sample wells organized in rows and columns, with a predetermined number of sample wells in a column, the method comprising:
positioning the sample plates end to end so that corresponding columns of adjacent sample plates align;
arranging a plurality of fluid dispensers into a generally linear array of fluid dispensers arranged in a column direction, where each fluid dispenser is configured to dispense fluid into individual wells of the sample plates, where the array of fluid dispensers has a footprint in the column direction, where each of the sample plates has a footprint in the column direction, where the footprint of the array of fluid dispensers in the column direction is longer than the footprint of any single one of the sample plates in the column direction;
positioning at least some of the fluid dispensers in the array of fluid dispensers with reference to a first column of sample wells;
dispensing a predetermined volume of a material into selected sample wells in the first column from at least some of the fluid dispensers;
moving the array of fluid dispensers in a row direction so that at least some fluid dispensers in the array of fluid dispensers are positioned with reference to a second column of sample wells; and
dispensing a predetermined volume of a material into selected sample wells in the second column from at least some of the fluid dispensers.

100. The method of preparing mother liquors according to claim 99, wherein each fluid dispenser has an associated material, and all fluid dispensers in the array of fluid dispensers dispense an associated liquid substantially simultaneously in both the first and second dispensing steps.

101. The method of preparing mother liquors according to claim 100, wherein the first and second columns span a plurality of the sample plates.

102. The method of preparing mother liquors according to claim 99, further including the step of continuing to move the array of fluid dispenser and dispense a volume of liquid into selected sample wells until at least one fluid dispenser has been positioned directly above each of the sample wells in a row.

103. The method of preparing mother liquors according to claim 99, further including the steps of:
advancing the plurality of sample plates to a next row position; and
moving the array of fluid dispensers and dispensing a volume of liquid into selected sample wells while the sample plates ar positioned in the next row position.

104. The method of preparing mother liquors according to claim 99, further including the step of dispensing different liquids from adjacent fluid dispensers in the away of fluid dispensers.

105. The method of claim 99, wherein the plurality of fluid dispensers are configured so that at least two multi-well holders can be beneath the plurality of fluid dispensers at the same time.

106. The method of claim 99, wherein the plurality of fluid dispensers are configured so that at least three multi-well holders can be beneath the plurality of fluid dispensers at the same time.

107. The method of claim 99, wherein the plurality of fluid dispensers are configured so that at least four multi-well holders can be beneath the plurality of fluid dispensers at the same time.

108. The method of claim 99, wherein the plurality of fluid dispensers are configured so that the fluid dispensers can deliver the material to at least two multi-well holders at the same time.

109. The method of claim 99, wherein the plurality of fluid dispensers are configured so that the fluid dispensers can deliver the material to at least tree multi-well holders at the same time.

110. The method of claim 99, wherein the plurality of fluid dispensers are configured so that the fluid dispensers can deliver the material to at least four multi-well holders at the same time.

111. The method of claim 99, wherein the plurality of fluid dispensers are configured so that all of the fluid dispensers can deliver the material at the same dime.

112. The method of claim 99, wherein the sample plates am on a moving element that has a length of at least n of the sample plates, wherein n is the number of the multi-well plates, wherein each of the multi-well plates has m wells, wherein m is the number of wells, wherein the method processes one of the multi-well plates every m dispensings even though the method involves n times m dispensings.

113. The method of claim 112, wherein the sample plates are on a moving element that has a length of at least two multi-well plates, wherein each multi-well plate has 96 wells.

114. The method of claim 112, wherein the sample plates are on a moving element that has a length of at least three multi-well plates, wherein each multi-well plate has 96 wells.

115. The method of claim 112, wherein the sample plates are on a moving element that has a length of at least four multi-well plates, wherein each multi-well plate has 96 wells.

116. The method of claim 99, wherein a controller directs the delivery of the material from one or more fluid containers to each of the sample plates.

117. The method of claim 116, wherein the controller directs the delivery of the material from each of at least eight fluid container to each of at least two multi-well plates.

118. The method of claim 116, wherein the controller directs the delivery of the material from each of at least eight fluid containers to each of at least three multi-well plates.

119. The method of claim 116, wherein the controller directs the delivery of the material from each of at least eight fluid contain to each of at least four multi-well plates.

* * * * *